United States Patent [19]

Antle et al.

[11] Patent Number: 4,468,331

[45] Date of Patent: Aug. 28, 1984

[54] METHOD AND SYSTEM FOR LIQUID CHOROMATOGRAPHY SEPARATIONS

[75] Inventors: Paul E. Antle, Newark, Del.; John A. Schmit, Elkton, Md.; Edward L. Smith, Jackson, N.J.

[73] Assignee: E. I. Du Pont de Nemours and Company, Wilmington, Del.

[21] Appl. No.: 417,519

[22] Filed: Sep. 13, 1982

[51] Int. Cl.³ .............................................. B01D 15/08
[52] U.S. Cl. .................................... 210/659; 210/746; 210/198.2
[58] Field of Search ............ 210/635, 659, 656, 198.2, 210/746

[56] References Cited

U.S. PATENT DOCUMENTS

| | | | |
|---|---|---|---|
| 4,042,499 | 8/1977 | Ramstad et al. | 210/659 |
| 4,128,476 | 12/1978 | Rock | 210/656 |
| 4,199,450 | 4/1980 | Dulout et al. | 210/656 |
| 4,233,156 | 11/1980 | Tsukada et al. | 210/198.2 |
| 4,311,586 | 1/1982 | Baldwin et al. | 210/198.2 |

OTHER PUBLICATIONS

Berridge, J. of Chromatography, pp. 1-14 (1982).
Drouen, et al., Chromatographia, vol. 16, pp. 48-53 (1982).
Antle, Chromatographia, vol. 15. pp. 3-7 (1982).
Lehrer, American Laboratory (1981).
Sentinel TM System (Du Pont Literature E-45870 (3/82).
Sentinel TM System Technical Report (Du Pont Literature E-45871).
Sentinel TM System Technical Report (Du Pont Literature E-49102) (3/82).
Snee, Chemtach, pp. 702-710, (1979).
Glajch, et al., J. of Chromatography, pp. 57-59 (1980).
Glajch, et al., J. of Chromatography, pp. 269-280 (1982).
Schoenmakers, A Systematic Approach to Mobile Phase Effects in Reversed Phase Liquid Chromatography (1981).
Issaq, J. of Liquid Chromatography, pp. 2091-2120 (1981).
Berridge, Chromatographia, vol. ly, pp. 172-175 (1982).
Microprocessor-Based Instrumentation by Garton, CEP Nov. 1981 pp. 44-49.

*Primary Examiner*—John Adee

[57] ABSTRACT

A microprocessor-based analytical liquid chromatograph is programmed to run automatically a series of experiments on a sample mixture using four solvents to determine the solvent strengths and composition needed to optimize resolution.

3 Claims, 18 Drawing Figures

SEPARATE

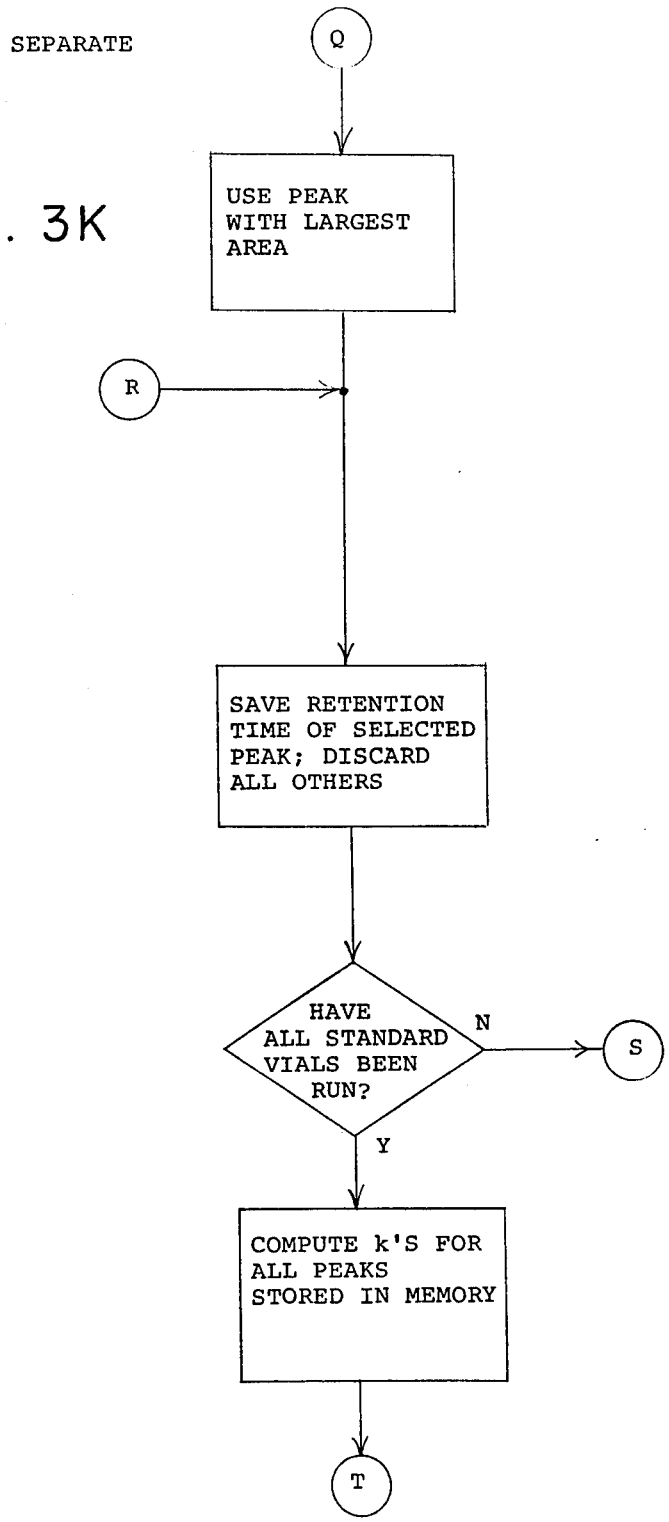

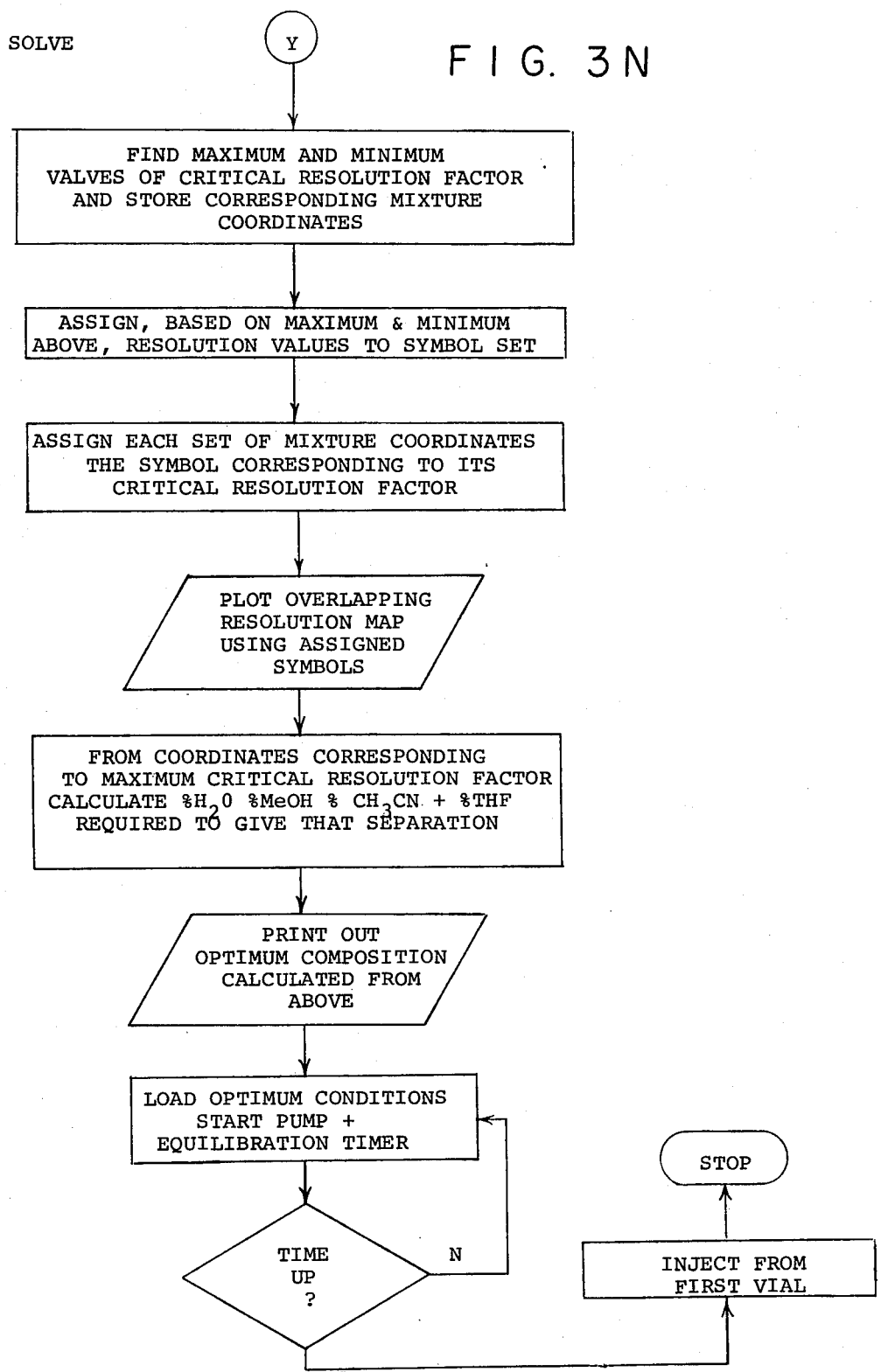

— · — · — Reverse - phase
------- Normal - phase

METHOD AND SYSTEM FOR LIQUID CHOROMATOGRAPHY SEPARATIONS

BACKGROUND OF THE INVENTION

This invention relates to liquid chromatography and more particularly to an automated system for performing isocratic interactive high performance liquid chromatographic separations and finding the optimum mobile phase strength and selectivity for use in such separations.

Liquid chromatography (LC) is a technique capable of separating a sample mixture into its components. The sample is transported through a separating column, using a mobile phase carrier, which resolves or separates the sample components such that they elute from the column in seriatim. A detector provides an electrical signal in response to each component, which signal appears graphically as a peak.

Chromatographic resolution of the components or peaks is dependent on many factors. Three primary factors that contribute to resolution ($R_s$) are relative retention ($K'$), separation selectivity ($\alpha$), and column efficiency ($N$). The factors are related to resolution by the equation $$R_s = \frac{\sqrt{N}}{4} \quad \frac{k'}{k+1} \quad \frac{\alpha - 1}{\alpha} \tag{1}$$

The mobile phase composition has a dominant influence on retention and selectivity. Changes in the mobile phase strength primarily affect the retention. Changes in the ingredients used in the mobile phase affects the specific chemical interactions in the resultant separation and therefore the selectivity. In the past, mobile phase strength and especially selectivity were adjusted empirically with an open-ended approach.

Chemical data is now available which classifies mobile phase solvents used in reverse phase and bonded phase LC according to the several selectivity interactions; proton acceptor, proton donor and dipole interaction. Similar data is available for the selectivity interactions or localization effects that affect separations in liquid-solid chromatography. These effects include a nonlocalizing solvent, a basic localizing solvent, and a nonbasic localizing solvent. These interactions are summarized in a so-called "selectivity triangle" with each apex representing one of the interactions. Mobile phase solvents are located within the triangle according to the relative contributions of these three interactions to the total solvent strength. Conversely, the location of each solvent is indicative of its selectivity effect.

This "selectivity triangle" has been used as the basis for rational solvent selectivity determinations. Recently, Glajch, Kirkland, Squire and Minor showed, in their article *Optimization of Solvent Strength and Selectivity for Reversed-Phase Liquid Chromatography* (J. Chromatogr. 199, 57 (1980)), an efficient and systematic technique for optimization of the mobile phase selectivity $\alpha$ for reversed phase LC separations. This technique uses four solvents, one from each apex of the selectivity triangle and a diluent, in various blends, which exhibit different selectivity but maintain constant retention $K'$, to perform seven experiments. The computerized mapping technique used to facilitate finding the optimum solvent blend for the mobile phase is based on Snee (*Experimenting with Mixtures*, Chemtech, 9 (Nov.), 702 (1979)).

Even with these prior art techniques, it was difficult and time consuming to select the proper solvent strength (composition) for a particular retention. And since this selection had to be made for each of the three selectivity solvents, it became a slow and inefficient manual operation. In addition, for each of the seven experiments, the total number of sample injections required is one plus the number of components in the sample mixture. This also increased the time required. As a result, most chromatographers did not adopt these techniques and many separations were effected under less than desirable conditions. In those cases where proper conditions were attained, many more experiments than necessary were usually performed to determine such conditions.

SUMMARY OF THE INVENTION

Accordingly, it is an object of this invention to improve this traditional approach. The methods development procedure has been reduced to a series of logic steps to rapidly and systematically scout first mobile phase strength and second selectivity with a closed end approach. Third, this procedure has been automated which further increases its speed. And, fourth, the data from the scouting experiments is automatically evaluated to find the optimum mobile phase conditions and run the separation using such conditions.

The invention is a method and system for improving isocratic LC separations using improved logic and equations, a plurality of selectivity adjusting solvents, and system automation. Physically, the system is comprised of: a pump module; a source of supply for the solvents connected to the input of the pump module; a separating column connected to the output of the pump module; and automatic sampler module coupled to introduce samples to the input of the column; a detector connected to the output of the column, and a controller module coupled to the pump module, the automatic sampler and to the detector. The controller also contains methods development and automation software for determining the optimum mobile phase composition and precisely controlling the operation of the system using such composition.

Using the method and/or system of this invention the user can automatically obtain the isocratic mobile phase composition required for optimum separation of all of the components in a complex sample mixture given a set of starting conditions. They may be used for either reversed phase or normal phase chromatography and are based upon the use of four solvents and results in an optimization of solvent strength and selectivity. This results in significantly increased speed of methods development and provides faster, more accurate analyses, all on an automatic basis without the direct intervention of a human operator. In one aspect of the invention, the controller determines mobile phase composition to provide a chosen value of retention for each of the three binary mixtures. Alternatively, or as a later step in the procedure the controller automatically scouts mobile phase compositions to find the optimum selectivity. The controller automatically adjusts the mobile phase solvent composition to provide a chosen value of retention and with such retention to provide optimum solvent selectivity or optimum resolution in a sample separation. Also, the controller identifies elution orders of the sample components in the seven liquid chromatographic experiments.

Figure 3:
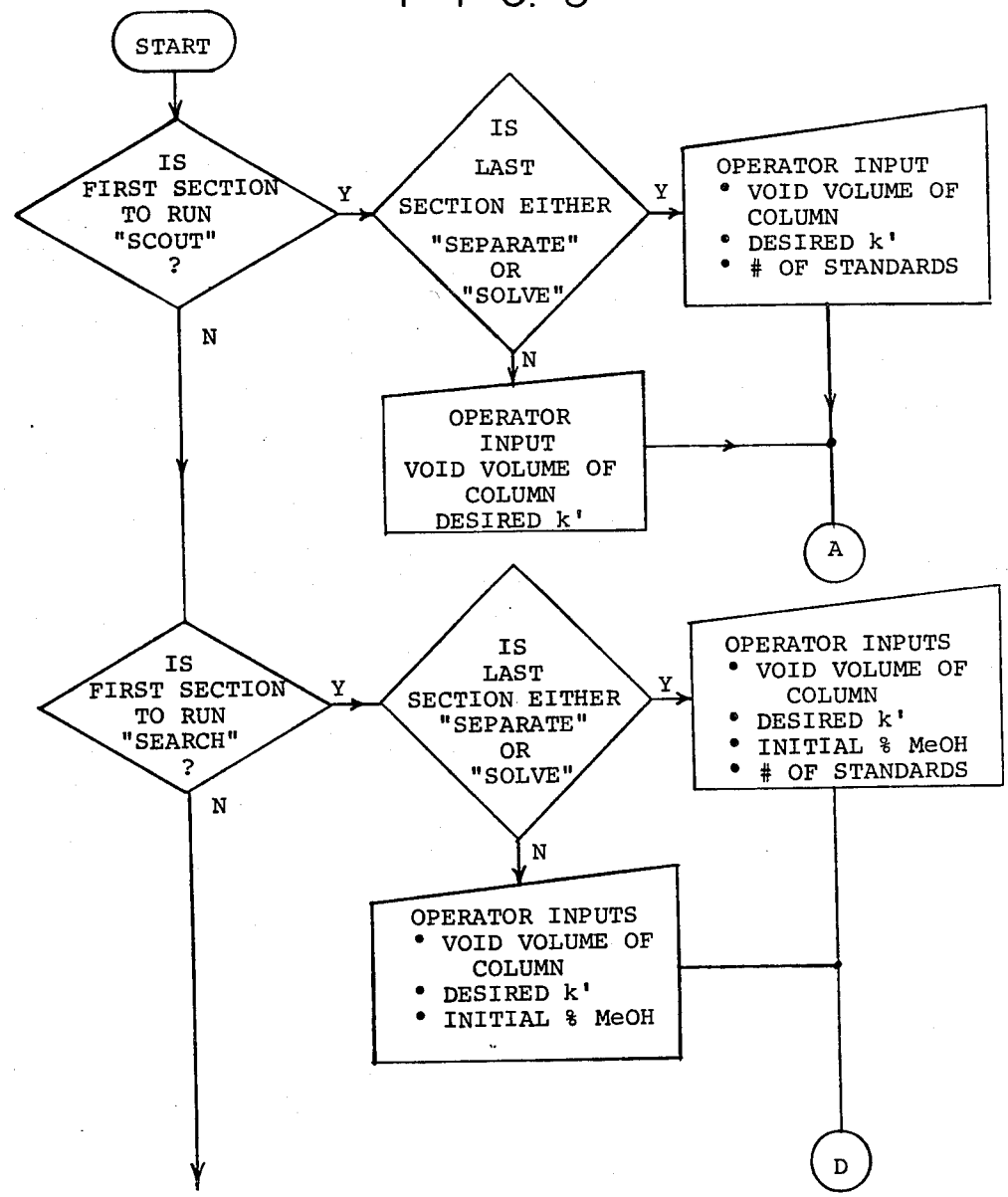
FIGS. 3–3N are flow diagrams of the various programs used to operate a preferred embodiment of this invention.
Figure 3:
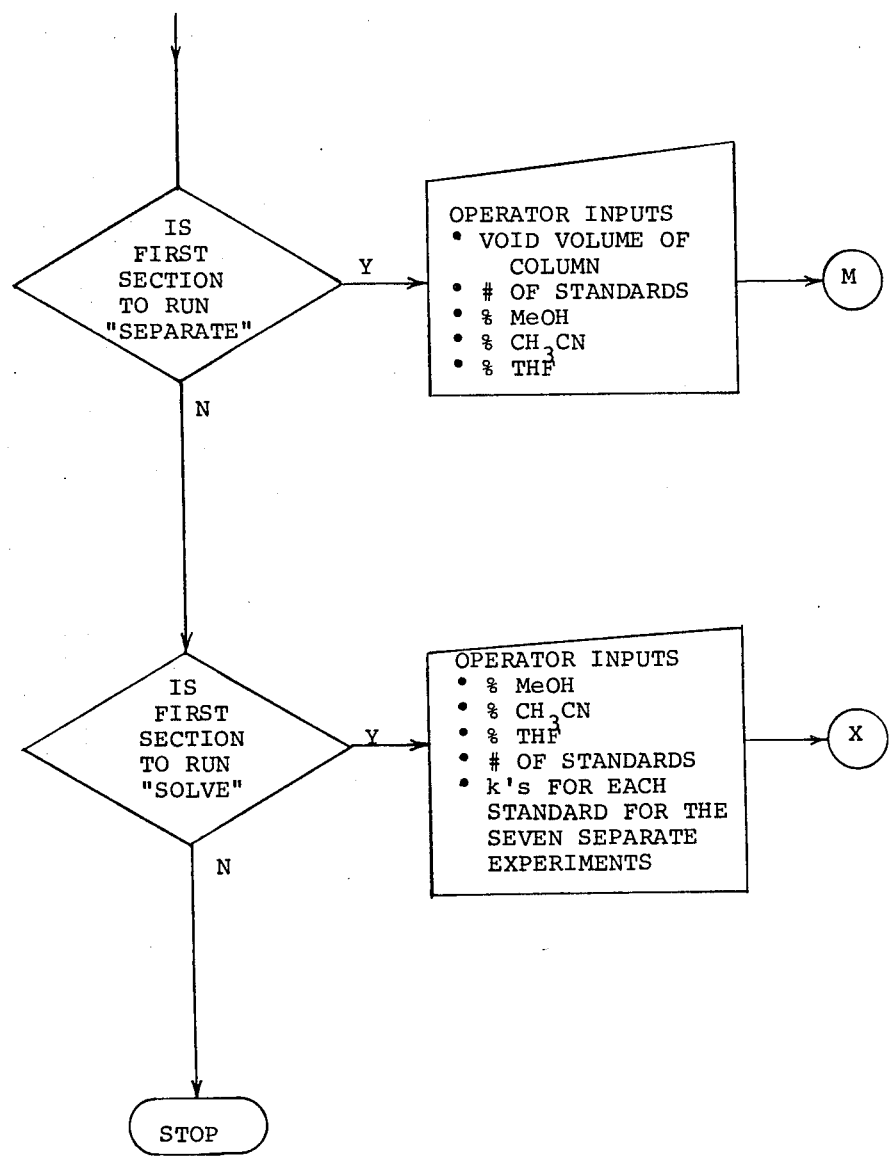

There is attached hereto Appendix I which is a program listing Basic of a program used to implement the method and system of this invention as described in the flow diagram of FIGS. 3–3N. "AUTOST" provides the user imputs described in this application as part of the SAMPLE section. In addition "DOWNLD" and 4100 contained basic calculations required throughout all the sections. "EQUIL2" is a subroutine which is taught any time the column is to be equilibrated. The SCOUT, SEARCH and SOLVE programs correspond directly with the SCOUT, SEARCH and SOLVE sections described in this application. The SEPARATE section is a combination of the programs labeled %B, C, D and SORT.

DETAILED DESCRIPTION OF THE PREFERRED EMBODIMENT

Figure 1:
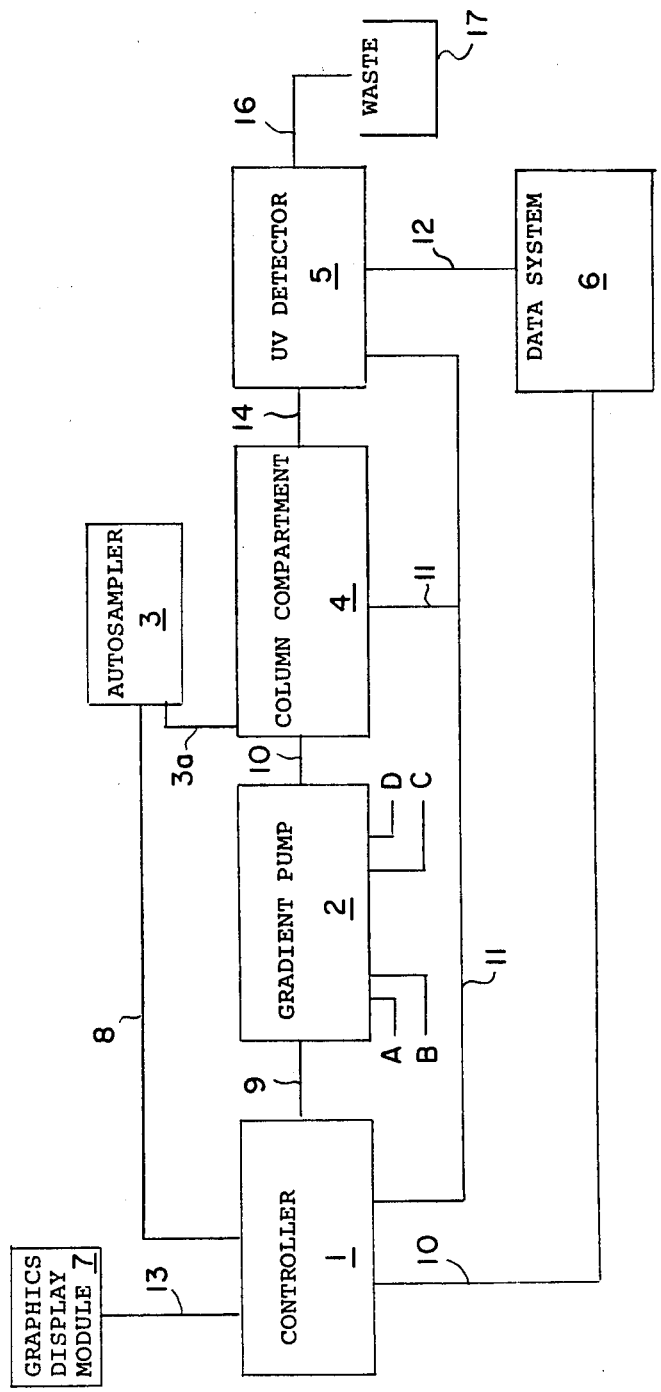
FIG. 1 is a block diagram of the chromatographic system of the invention.

Referring to FIG. 1, there is seen an LC system that may be used in performing the method of this invention. The system includes as its main elements a controller module 1, a pump module 2, a column module, an automatic sampler 3 and a conventional LC detector 5 such as an absorbance detector. The controller 1 is a microprocessor-based instrument which provides timing signals for solenoid valves and drive signals for a stepper drive motor for the pump in the pump module 2 via cable 9. Communications between controller 1, column compartment 4 and detector 5 are accomplished using a general purpose interface bus 11. The controller 1 provides sample injection pulses and timing control to the autosampler 3 via cable 8. Communications between controller 1 and data system 6 is accomplished via cable 10 using a standard current loop configuration. The data system 6 receives an analog signal from the detector 5 via cable 12 whose signal level (a peak) represents the absorbance or concentration of a sample component entrained in the mobile phase passing through the detector cell. It converts the analog signal into digital form and stores it until needed by the controller. All of the components are of conventional design and are available commercially from various vendors. The controller 1 provides visual information to the operator via the graphics display module 7. Displayed information is sent over cable 13.

As noted above, it is possible to obtain selected retention times and to optimize either the selectivity or the resolution of LC separations by adjusting the makeup and strength of the mobile phase. The adjustments and their relation to the LC system may be better understood with reference to FIGS. 2, 3, 4 and 5. In these figures, the quaternary solvents used to make up the mobile phase are derived each of four separate solvent reservoirs designated in FIG. 2 by the letters A, B, C, and D respectively. It is known from equation (1) that the resolution $R_s$, which is a quantitative measure of the relative separation of the peaks, is a function of column efficiency N, retention k', and selectivity $\alpha$. The retention k' is a function of mobile phase solvent strength whereas the selectivity factor $\alpha$ is a measure of chemical difference between the solvent components of the mobile phase. It is these two factors which are automatically varied by the system and method of this invention to achieve the desired retentions and optimizations.

L. R. Snyder in his article in J. Chromatographic Science, volume 16, page 223 (1978) developed a selectivity classification triangle which positions solvents within the triangle according to the solvent's contribution to the three factors at the apices of the triangle to the total solvent strength. The apices of the triangle are determined in the case of reverse and bonded phase LC by proton acceptor, proton donor and dipole interaction as may be seen in FIG. 4. For the liquid-solid LC selectivity triangle (not shown), the apices represent the selectivity factors nonlocalizing solvent (methylene chloride-$CH_2Cl_2$), a basic localizing solvent (methytertbutyl ether-MTBE) and a nonbasic localizing solvent (acetonitrile-ACN). Hexane may be used as the fourth or strength-adjusting solvent.

Figure 4:
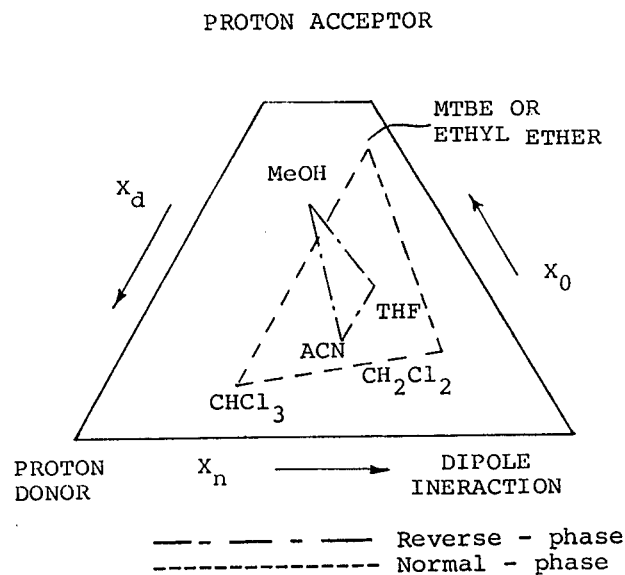
FIG. 4 is a solvent selectivity triangle for solvents used in reverse phase and normal bonded phase chromatography.

In order to optimize solvent selectivity, these solvents are selected from groups near the respective apices of the triangle in order to obtain large differences in the selectivities of the solvents. The solvents are blended to obtain intermediate selectivities. The three selectivity adjusting solvents for normal phase chromatography are ether-MTBE, methylene chloride-$CH_2Cl_2$, and chloroform-$CHCl_3$. The fourth or strength adjusting solvent is hexane. These are shown interconnected by dashed lines. The three solvents typically used for reverse phase chromatography, methanol-MeOH, tetrahydrofuran-THF, and acetonitrile-ACN, are shown in FIG. 4 connected by the dash dot lines. In this instance the strength adjusting solvent is water.

Figure 2:
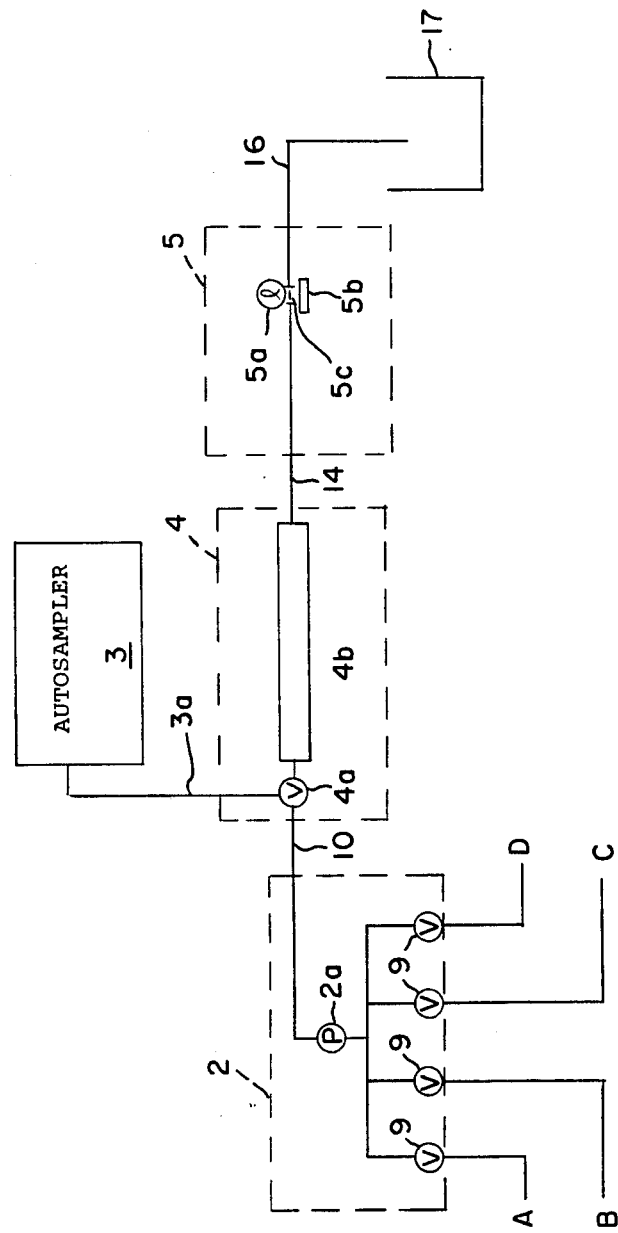
FIG. 2 is a schematic diagram of the solvent system of this invention.

These respective groupings of four solvents thus make up the several inputs A, B, C, D of FIG. 2. By convention, for reverse phase chromatography, the strength adjusting solvent is solvent A, solvent B is the strongest proton acceptor solvent, solvent C is the strongest proton donor, and solvent D is the strongest dipple interactor. Thus for reverse phase separations, water is A, MeOH is B, ACN is C, and THF is D. A similar convention is used for other types of chromatography. These solvents are introduced on a timed basis by solenoid valves 9 and mixed. The resulting composition is dictated by the relative open time of each valve and is brought to high pressure by the pump 2a. The solvent stream passes through connecting tubing 10 to the injection valve 4a in column compartment 4. A liquid sample from the autosampler 3 is introduced into the liquid stream from the pump 2a via line 3a and injection valve 4a. When the valve is actuated, the sample passes through the separating column 4b. If the components of the sample each have different affinities for the packing material contained in the column 4b, the output of the column is a band of each component, each having a particular retention on the column.

The output of the column is passed through tubing 14 to the detector 5. In the preferred embodiment, this includes an ultraviolet lamp 5a, a photodiode assembly 5b and an aperture 5c positioned between the lamp and the photodiode assembly. Using this detector, the output of the column is irradiated by the ultraviolet lamp 5a whose output is filtered in a band centered at 254 nanometers. The photodiode assembly 5b measures the amount of ultraviolet light passing through the aperture 5c. As each sample component passes through the detector, the resulting ultraviolet level at the photodiode assembly 5b changes. The photodiode assembly output is converted to an analog voltage representing the peak or sample component. The sample is then passed through tubing 16 to a waste container 17.

The method and system of this invention perform what may be grouped into five different modes of operation. The first mode, designated SAMPLE, provides automatic injection and automatic sampling as required during the following four steps. Also during this mode, the operator introduces into the system, through the microprocessor, the desired column and solvent equilibration times, analysis times and data acquisition functions that he desires.

The next operational mode, designated SCOUT, effects a standard gradient run using one of the solvents depicted in FIG. 4 for the selected type of chromatography. Based on this gradient run, the peak retentions obtained are examined and translated to corresponding isocratic conditions. The desired retention range of the sample is inputted to the microprocessor in the controller in terms of the retention factor of the last sample peak. The controller uses a novel routine to predict the isocratic solvent composition required for the desired retention factor. The particular relationship used in making this conversion will be discussed in the following sections in an example using reverse phase chromatography.

The next operational mode, designated SEARCH, sets up the experimental conditions established during the SCOUT routine and chromtographs the sample with the initial solvent pair selected and compares the data obtained with the desired value of the retention factor. If the actual retention factor K' is not within the desired range, the system used the data from the first separation to recalculate and establish the next solvent composition to produce the desired k'. When an acceptable retention factor k' is obtained for the first solvent, the equivalent solvent strength for the remaining two solvents is then calculated using the equation $S_t = \Sigma S_i \phi_i$ where $S_t$ is the total solvent strength, $S_i$ are the solvent strength weighting factors for each component and $\phi_i$ are the volume fractions of each component. The %B is equal to 100 times $\phi_B$. Experiments are performed to verify the predictions and recalculate as above.

Figure 5:
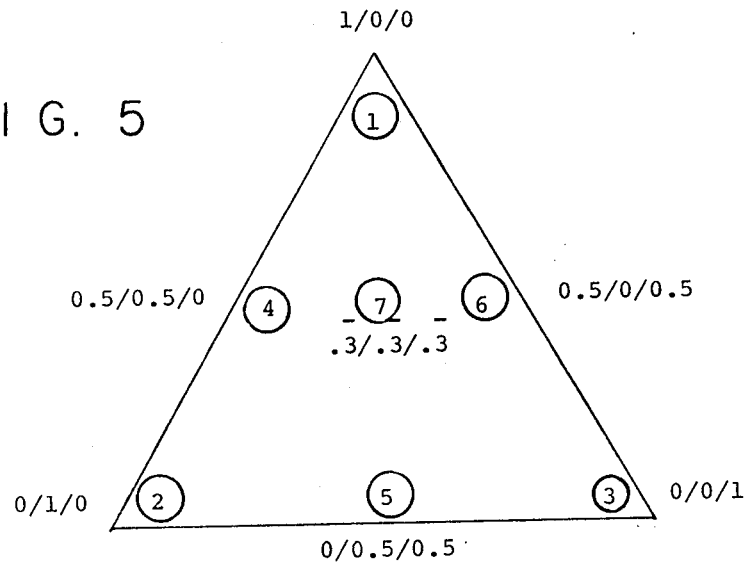
FIG. 5 is a solvent optimization triangle showing seven experiments needed to optimize LC resolution.

In the next operational mode, SEPARATE, the retention time of each component contained in the sample mixture is determined for each of the seven mobile phase blends described in the method development triangle depicted in FIG. 5 as taught by Glajch et al. The compositions of the mobile phase, as represented by the apices of the triangle, are calculated from the results of the prior SEARCH mode of operation. Experiments 4, 5 and 6 use ternary mobile phases which are calculated from the three predetermined binary mobile phases taken two at a time. For example, in FIG. 5, the series of three members refer to the relative contribution of the three selectivity solvents B, C and D to the total selectivity, i.e., the ternary mobile phase at point 6 is made up of half of mobile phases Nos. 1 and 3. The condition used in experiment 7 is a quaternary mobile phase whose composition is also calculated from the three binary mobile phases. The separations obtained from experiments 4 through 7 together with those from 1 through 3 provide a sufficient data base to generate a closed-ended optimization of the separation. The retention data obtained during the SEPARATE mode is used to identify the retention position of each compound in each experiment. SOLVE, the last operation, then uses this data to provide an overlapping resolution map (ORM) using conventional statistical computer routines for all peak pairs. These computerized mapping techiques are discussed by Snee in his article referred to above. Based upon this ORM map an optimum solvent composition for obtaining the optimum resolution for the overall separation can be predicted. The data generated during the four operational modes results in an automatically obtained analysis (SOLVE) of the sample under evaluation using optimum resolution conditions according to the desire of the operator.

In an alternative embodiment of the invention, using this same ORM map, a separation based on optimum solvent selectivity may be effected. This is accomplished by taking the data from the seven experiments and from this data calculating the retention behavior of each composition with any mobile phase composition described by the triangle. With this complete description of retention, either selectivity or resolution can be calculated. The optimization procedure searches for the maximum value of either resolution or selectivity. The predicted compositions may be different because the selectivity optimization ignores the effect of K' on resolution. Resolution is proportional to $K'/k' + 1$.

EXAMPLE

To better understand the particular mechanisms of these five operational modes, they will be explained in detail with respect to a reverse phase separation utilizing the solvents, methanol (MeOH), acetonitrile (CH$_3$CN) and tetrahydrofuran (THF) with water as the strength adjusting solvent.

FIGS. 3 through 3N contain the flow chart of a preferred controller program for automatically performing separations at optimum resolution. Also, Appendix I contains a listing of a computer program used to implement this flow chart. Turning to FIG. 3, the operator interface is shown. The controller program is divided into five distinct sections: SAMPLE, SCOUT, SEARCH, SEPARATE and SOLVE. Any individual program section or sequential combination is allowed to be run.

The operator's first action is to select the first and last modes or sections to be run. This is accomplished typically by positioning arrows on a graphics display module via the controller keyboard. Depending on the programs selected, the operator is prompted to provide the necessary inputs. Typical inputs during the SAMPLE mode include void volume of the column, desired k', number of standards to be run, initial % methanol (MeOH), initial % acetonitrile (CH$_3$CN), and initial % tetrahydrofuran (THF). Water is used as the strength adjusting solvent. The program then branches to FIG. 3A if SCOUT is the first section to run, to FIG. 3C if SEARCH is the first section to run, to FIG. 3H if SEPARATE is the first section to run, or to FIG. 3M if SOLVE is the first section to run. Further discussion is based on assumption that the entire program SCOUT through SOLVE will be run.

SCOUT

Figure 3A:
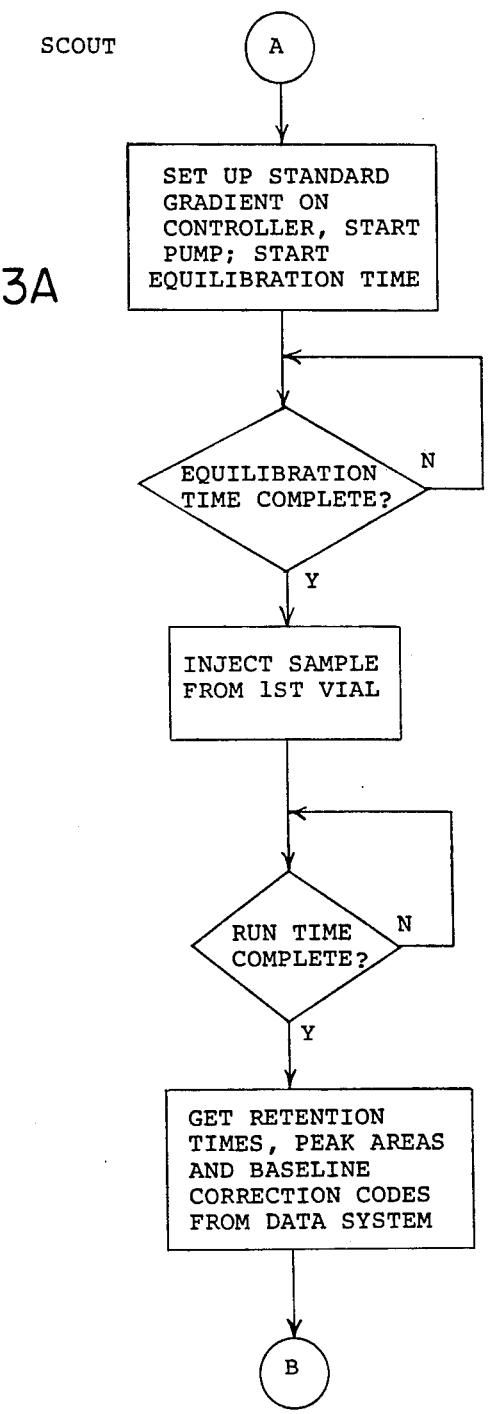

Referring to FIG. 3A, if SCOUT is to be run, the controller first sets up a standard gradient LC run consisting of a flow rate of 3 ml/min, oven temperature of 50° C. and linear gradient profile of 100% water to 100% methanol (one of the solvents of the solvent triangle) in 20 minutes and holding at 100% methanol for 10 minutes. These values are suitable for a majority of samples. In this illustrative example, it is assumed the sample contains the steroids Prednisone, Cortisone, Hydrocortisone, Dexamethasome, Corticosterone, and Cortexolone. The user is instructed that a Zorbax ® C-8 packed column (0.46×15 cm) is to be used for this step. The pump is started and an equilibration clock in the controller 1 begins runnings. When the equilibration clock reaches the preset time of a sample of the steriod mixture from the first vial is injected. The user has been instructed that the first sample vial must contain the sample mixture while the next six vials contain standard solutions of each of the steroids. The controller 1 starts measuring time since the injection was made. When 30 minutes has elapsed, the controller commands the data system to send the retention times, peak areas and baseline correction codes, derived from the gradient run and stored in the data system 6, to the controller 1.

Figure 3B:
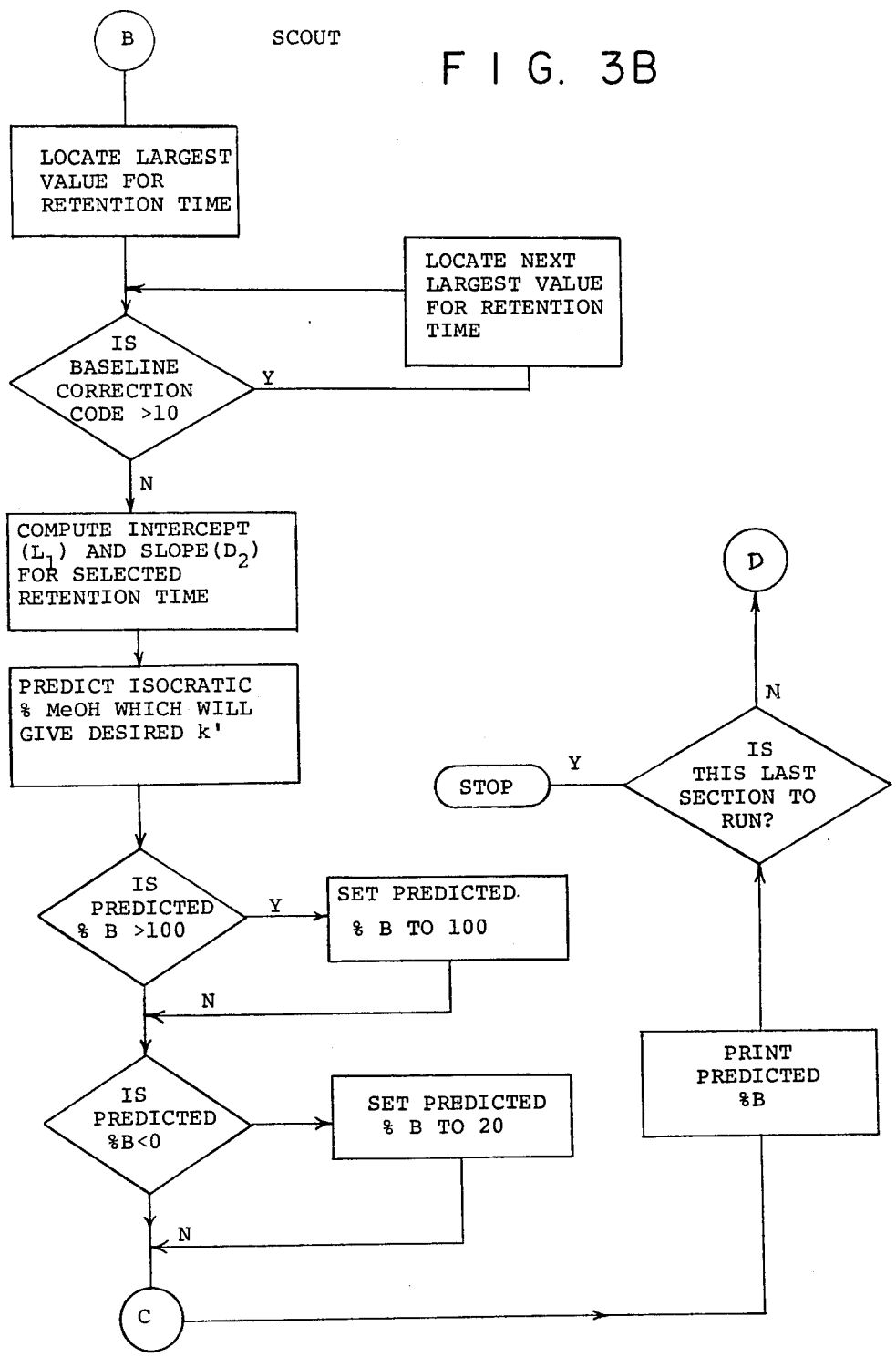

Turning to FIG. 3B, the flow chart indicates the controller finds the largest peak retention time $t_R$ that occurred during the gradient runs. When this is done, the controller checks the baseline correction code for that retention time. This is done to eliminate the possibility of baseline shifts or other effects from being counted as a peak. If the baseline correction code is greater than 10, which could occur for example if the largest retention time is caused by refractive index effects, the peak with the second largest retention time is selected for use in computations.

The next two calculations are carried out to define the linear dependence of the logarithm of isocratic retention ($k'$) on % methanol in the mobile phase. First, the Y-axis intercept ($L_1$) of the log $k'$ vs % MEOH plot is calculated using the formula:

$$L_1 = \text{intercept} = Ax^3 + Bx^2 + Cx - D \quad (1)$$

where
A=0.00233 B=−0.06118
C=0.63021
D=0.57685 and x=largest retention time.
The slope ($D_2$) of the log $k'$ vs % MeOH (or %B) plot (the line defining relationship between the retention and solvent strength) is now computed based on $L_1$ calculated from equation (1) as follows:

$$D_2 = (-0.01613) + (-0.007 * L_1). \quad (2)$$

Next, knowing the slope and the Y-axis intercept of the line defining this relationship, the isocratic % of methanol ($E_1$) necessary to obtain the desired $k'$ is predicted using the equation:

$$E_1 = ((\log(\text{DESIRED } K') - L_1)/D_2) \quad (3)$$

Note that all percentages calculated in this and other sections are adjustable to match the the instrument (e.g. 66.66666% is truncated to 66% for an instrument with a 1% minimum increment).

The predicted value of $E_1$ is first checked to see if it is more than 100%. If so the predicted value is set at 100%. Next, the predicted $E_1$ is checked to see if the % methanol in water predicted is less than zero. If so, a value of 20% methanol is used. % B is now determined.

The operator's selection of programs is examined. If SCOUT was to be the only program run, the controller prints its predicted % B, then stops. If not, the controller moves into the SEARCH section or mode.

SEARCH

Figure 3C:
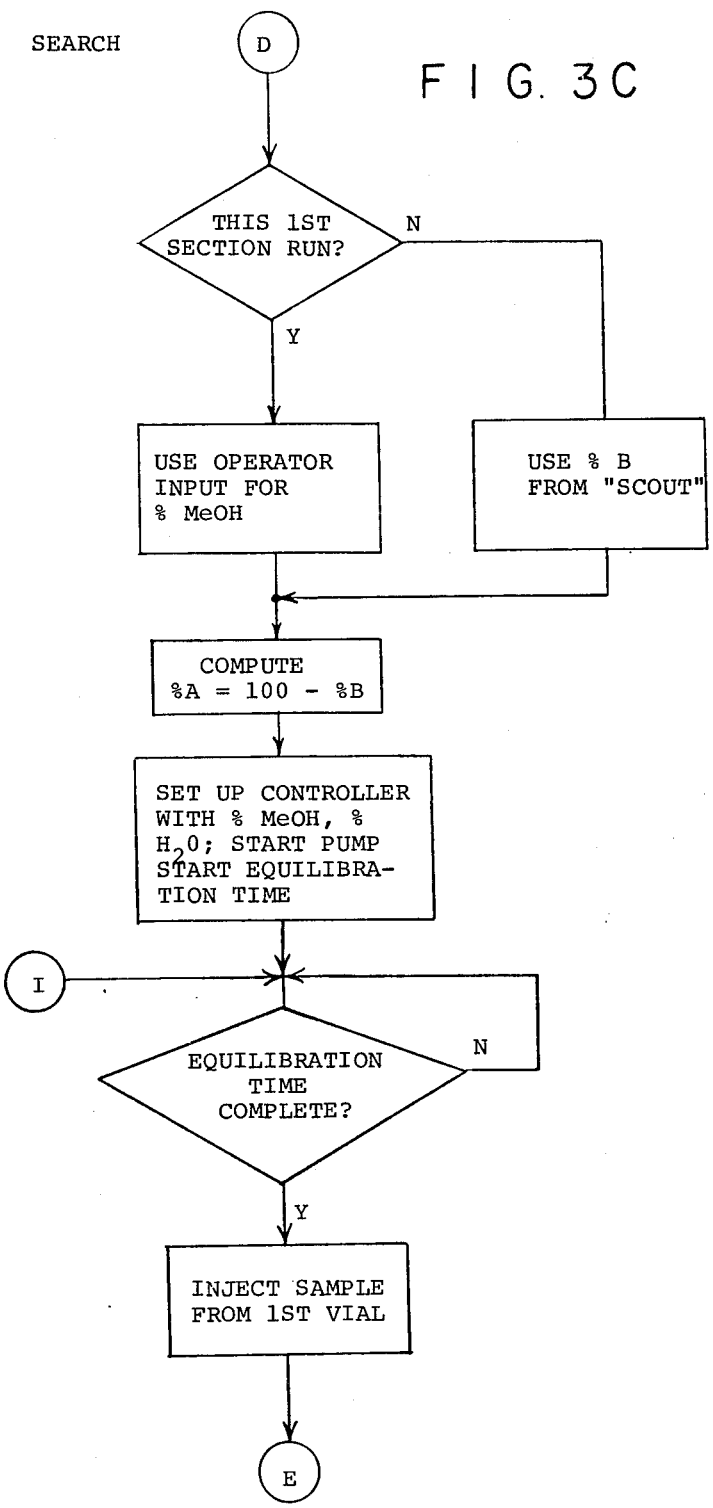

Referring to FIG. 3C, the first SEARCH operation performed is to check whether this is the first section run. If yes, the operator-supplied value for initial % methanol is used. If not, the predicted isocratic % methanol from SCOUT is used.

The controller now sets the % methanol and % water (100-% methanol) into the current conditions memory location and starts an equilibration timer. When the equilibration timer reaches a predetermined value, a sample is injected, again from the first sample vial and a run time clock begins.

Figure 3D:
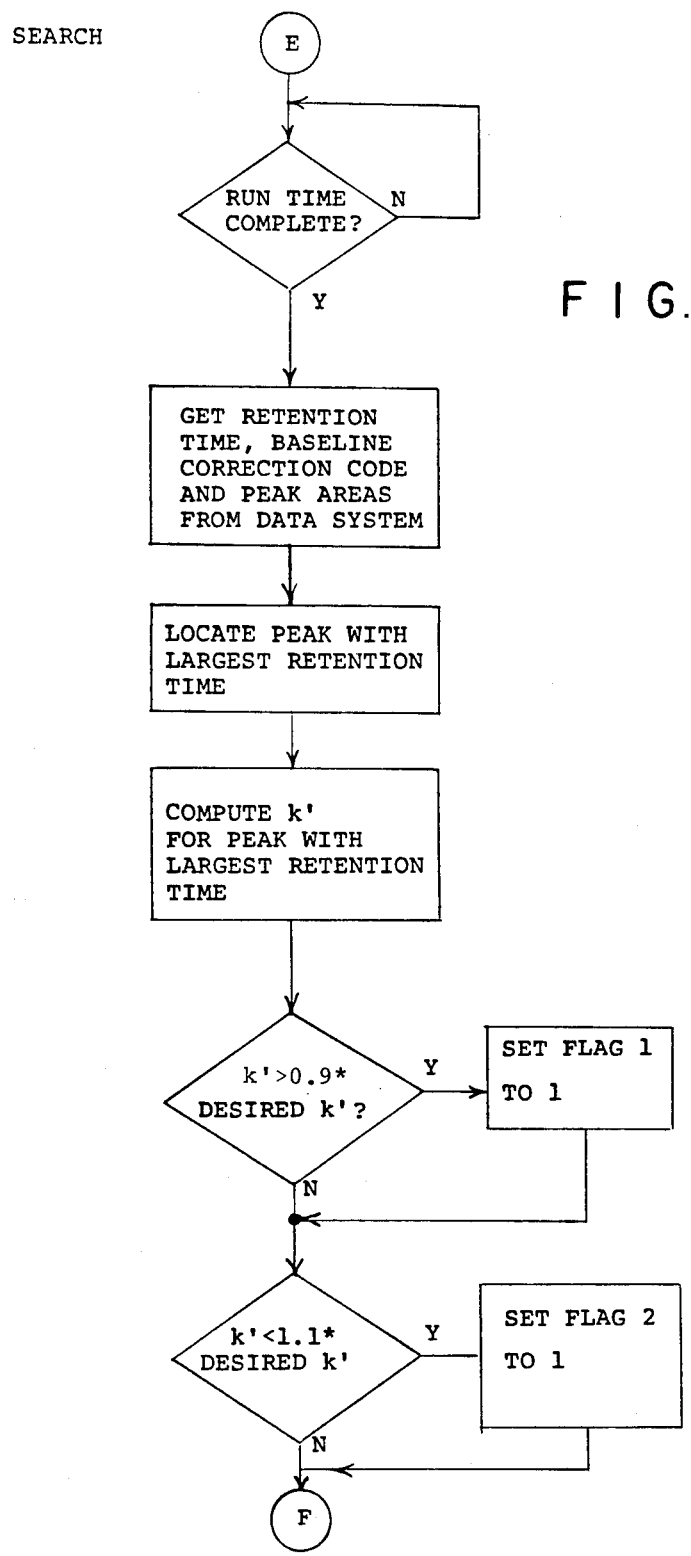

Turning to FIG. 3D, when the run time clock reaches its predetermined value, indicating completion of the run, the controller sends for the peak areas, retention times and baseline correction codes from the data system. The controller now computes the retention factor $k'$ for the peak with the largest retention time using the formula:

$$k' \text{ (result)} = \frac{\text{(RETENTION TIME)} - \text{(VOID TIME OF COLUMN)}}{\text{VOID TIME OF COLUMN}} \quad (4)$$

The $k'$ (result) is now compared to $k'$ (desired). If $k'$ (result) is greater than 90% of $k'$ (desired) Flag 1 is set to 1. If $k'$ (result) is less than 110% of $k'$ (desired) Flag 2 is set to 1.

Figure 3E:
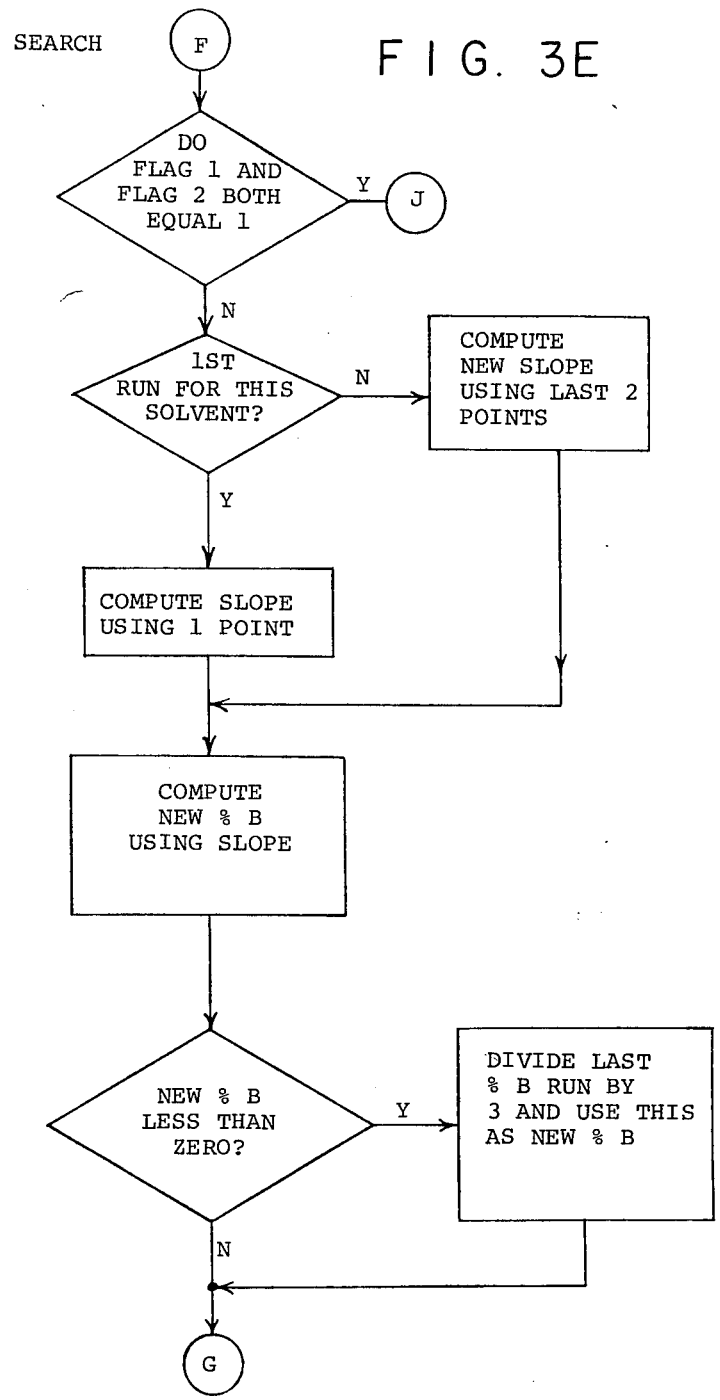

Referring to FIG. 3E, the status of Flags 1 and 2 is checked. If both are 1, then the $k'$ result) is considered to have satisfied $k'$ (desired). Under these circumstances, the program jumps to FIG. 3G. The first step is to identify which solvent conditions have been satisfied and to store the conditions. If the last $k'$ (result) was obtained under methanol/water conditions, the next combintation to be run is solvent C from the solventtriangle, i.e., acetonitrile/water. If the last $k'$ (result) was obtained from acetonitrile/water, then the next combination is the third solvent D from the solvent triangle, i.e., tetrahydrofuran/water. When another solvent is to be tested, the initial percent is calculated from the relative strength values, using the equation $S_T = \Sigma S_i \phi_i$ described previously. The program then returns to FIG. 3F. In the preferred embodiment, $S_A = 0$; $S_B = 2.67$; $S_C = 3.14$; and $S_D = 4.40$. This equation, when solved for the particular solvents of this exemplary program, is:

$$\phi_C = \frac{S_B \phi_B}{S_C}$$

$$\phi_D = \frac{S_C \phi_C}{S_D}$$

If the last run was tetrahydrofuran/water, then the SEARCH section ends since this is always the last combination to be run. Each value of the solvent composition which gives the desired $k'$ is stored as soon as it is verified.

Referring back to FIG. 3E, if the k' (result) does not satisfy the requirements of k' (desired) in the initial SEARCH run using methanol/water, a new value for the mobile phase strength must be determined. This is accomplished by redetermining the log k'-solvent strength linear relationship using the actual value of log k' obtained. Specifically, the slope of the new line is computed by assuming that the relationship between log k' and % B is linear and that equation (2) holds. Then the slope may be ascertained in terms of the log k' (result). If the k' (result) is the first k' obtained for the particular combination of mobile phases, this new slope is computed using the formula:

$$\text{Slope (new)} = \frac{\log k' \text{ (result)} + 2.297}{\% \text{ solvent} - 142.45} \quad (5)$$

If more than one result for a given mobile phase has been obtained, then the formula is:

$$\text{Slope (new)} = \frac{\log k' \text{ (result \#1)} - \log k' \text{ (result \#2)}}{\% \text{ solvent (result \#1)} - \% \text{ solvent (result \#2)}} \quad (6)$$

The next step is to predict a new value for the % methanol. First, we compute the new Y-axis intercept using the new slope using the formula:

$$\text{intercept (new)} = \quad (7)$$

$$\log k' \text{ (result)} - (\% \text{ solvent (result)}^* \text{Slope (new)})$$

The new solvent composition is computed using the following formula:

$$\% \text{ solvent (new)} = \frac{\log k' \text{ (desired)} - \text{intercept (new)}}{\text{Slope (new)}} \quad (8)$$

The % solvent (new) is tested to ensure that a value of less than 0 hasn't been computed. If it has, the % solvent used in the previous run is divided by 3 and used as the new % solvent.

Figure 3F:
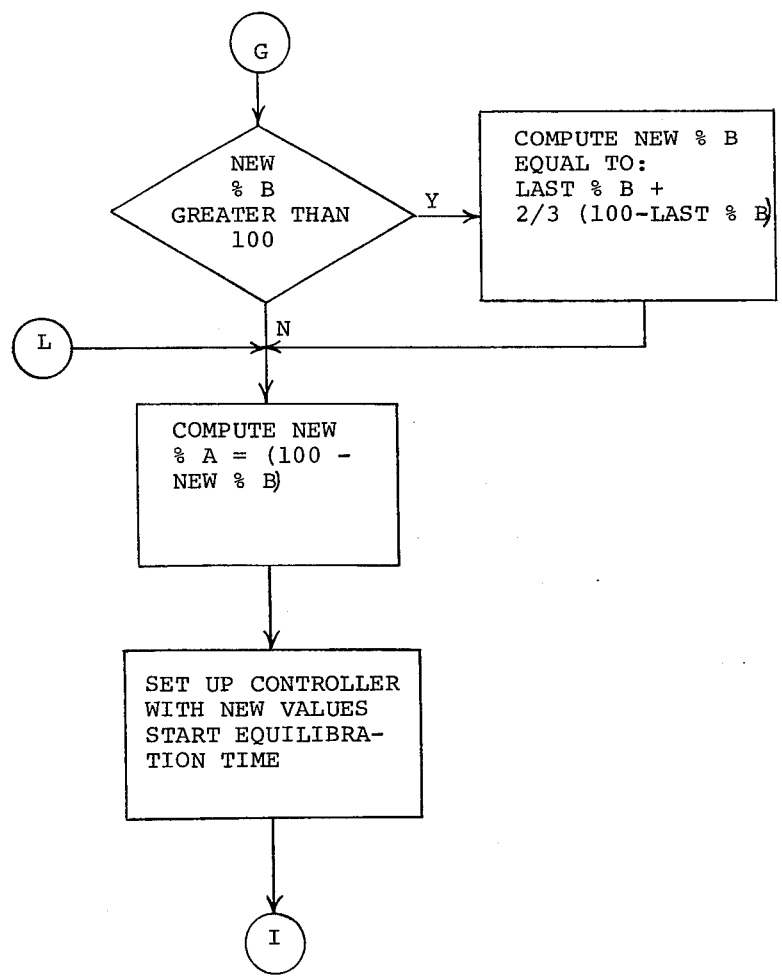

Turning to FIG. 3F, the % solvent (new) is tested for any value greater than 100%. If the value is greater than 100, then the % solvent (new) is computed by:

$$\% \text{ solvent (new)} = \quad (9)$$

$$\% \text{ solvent (last)} + \frac{(2^*(100 - \% \text{ solvent(last)}))}{3}$$

The next step is to find the 100's complement to the % solvent (new). When this is done, the computed conditions are loaded into current conditions memory and the equilibration timer started.

When the equilibration timer determines the end of the delay time (FIG. 3C), a sample is injected from the first sample vial and the entire process repeats.

Figure 3G:
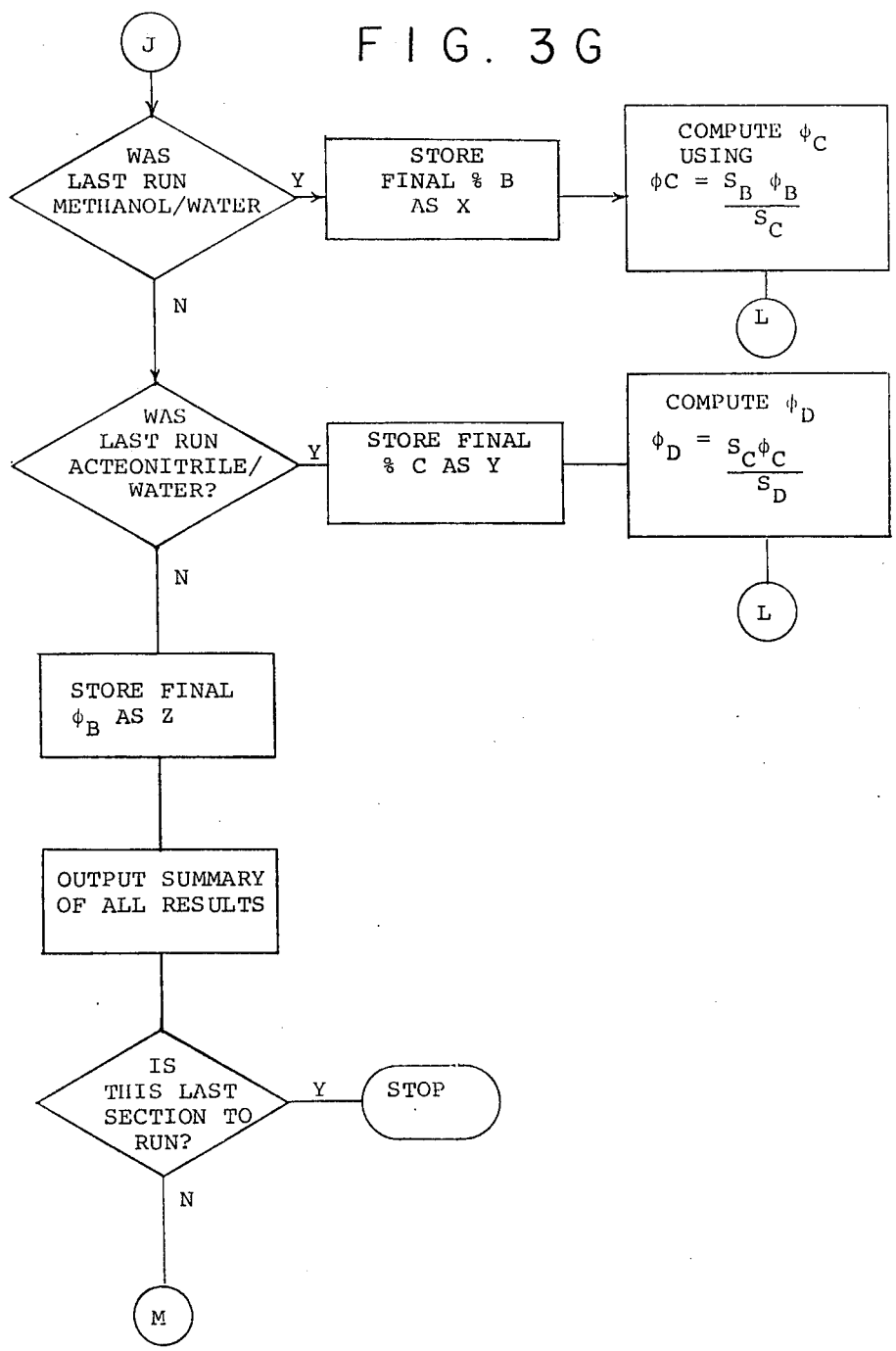

After all % solvents have been determined, the program shifts to FIG. 3G. A summary table is printed and the operator's inputs on FIG. 3 are examined. If the operator specified to run the SEPARATE section, the controller automatically proceeds to it (FIG. 3H), otherwise the program stops.

SEPARATE

Figure 3H:
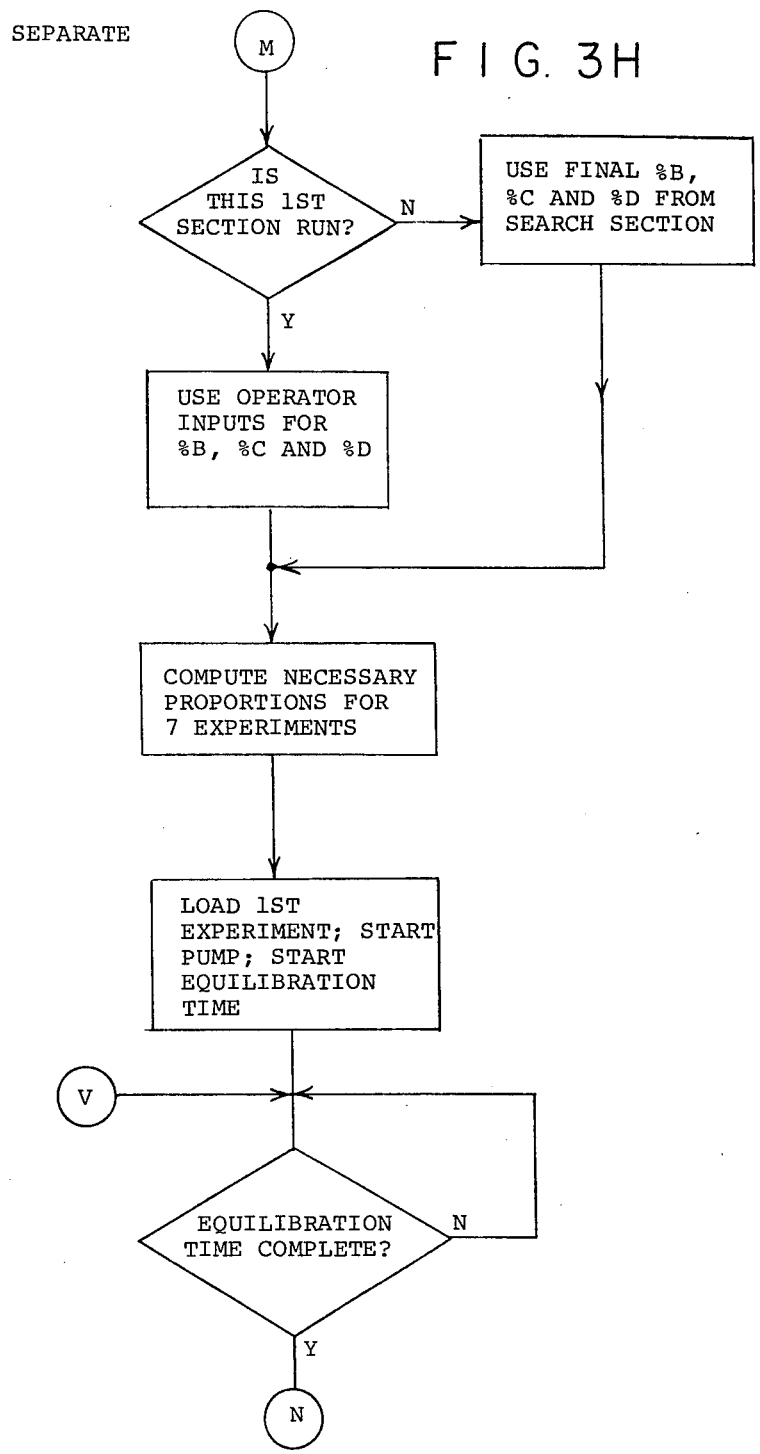
Figure 31:
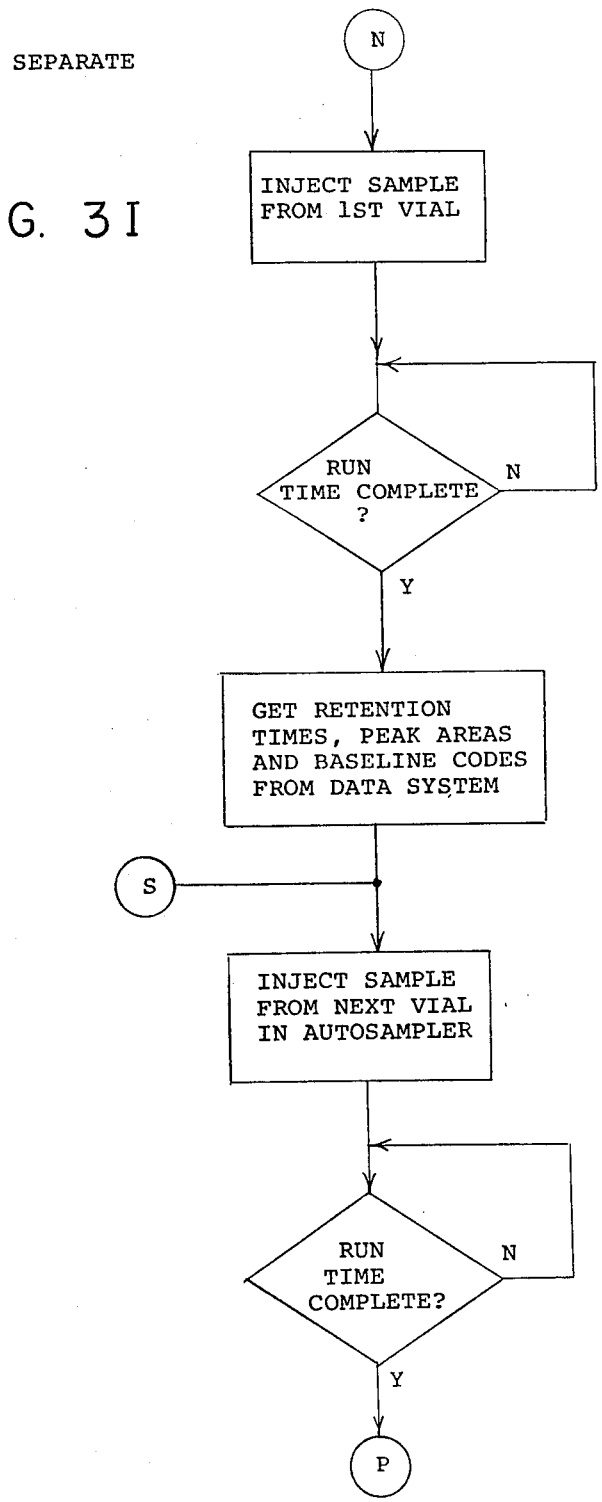

Referring to FIG. 3H, the SEPARATE section or mode of the software is shown. The first test is to determine if SEPARATE is the first section run. If it is, the operator-supplied values for % methanol, % acetonitrile and % tetrahydrofuran are used; otherwise the values determined in SEARCH are used.

The solvent compositions for all seven experiments are now computed and stored in the controller memory. The values of X, Y and Z are taken either from the operator's input or from SEARCH and ratioed according to the solvent triangle described in connection with FIG. 5. In the case at hand, these values would be:

| Experiment # | Methanol | Acetonitrile | Tetrahydrofuran |
|---|---|---|---|
| 1 | X | — | — |
| 2 | — | Y | — |
| 3 | — | — | Z |
| 4 | X/2 | Y/2 | — |
| 5 | X/2 | — | Z/2 |
| 6 | — | Y/2 | Z/2 |
| 7 | X/3 | Y/3 | Z/3 |

The water content in each experiment is the 100's complement of the sum of the % solvent used. The first experiment is loaded into current conditions memory, the pump started and an equilibration timer starts.

When the equilibration timer completes its timeout, a sample is injected (FIG. 3I) from the first sample vial and the run timer starts. This is the first sample vial position, in which the user has inserted the sample mixture. When the run timer is finished, the controller sends for the retention times, peak area and baseline correction codes from the data system and stores this information for later use.

For SEPARATE, unlike SCOUT or SEARCH, more than one vial is required in the autosampler. The first sample vial must contain the sample mixture, and subsequent sample vials must contain standard solutions of compounds found in the sample mixture. Flush vials, used to eliminate cross-contamination, can be present anywhere in the sequence.

The autosampler now moves to the next sample vial and makes an injection. The run timer reinitiates and runs until it times out. Upon timeout, the controller sends for the information from the data system. Since this is not the first vial, it must contain one component of the sample mixture and that component is assumed to be the major peak of the chromatogram.

Figure 3J:
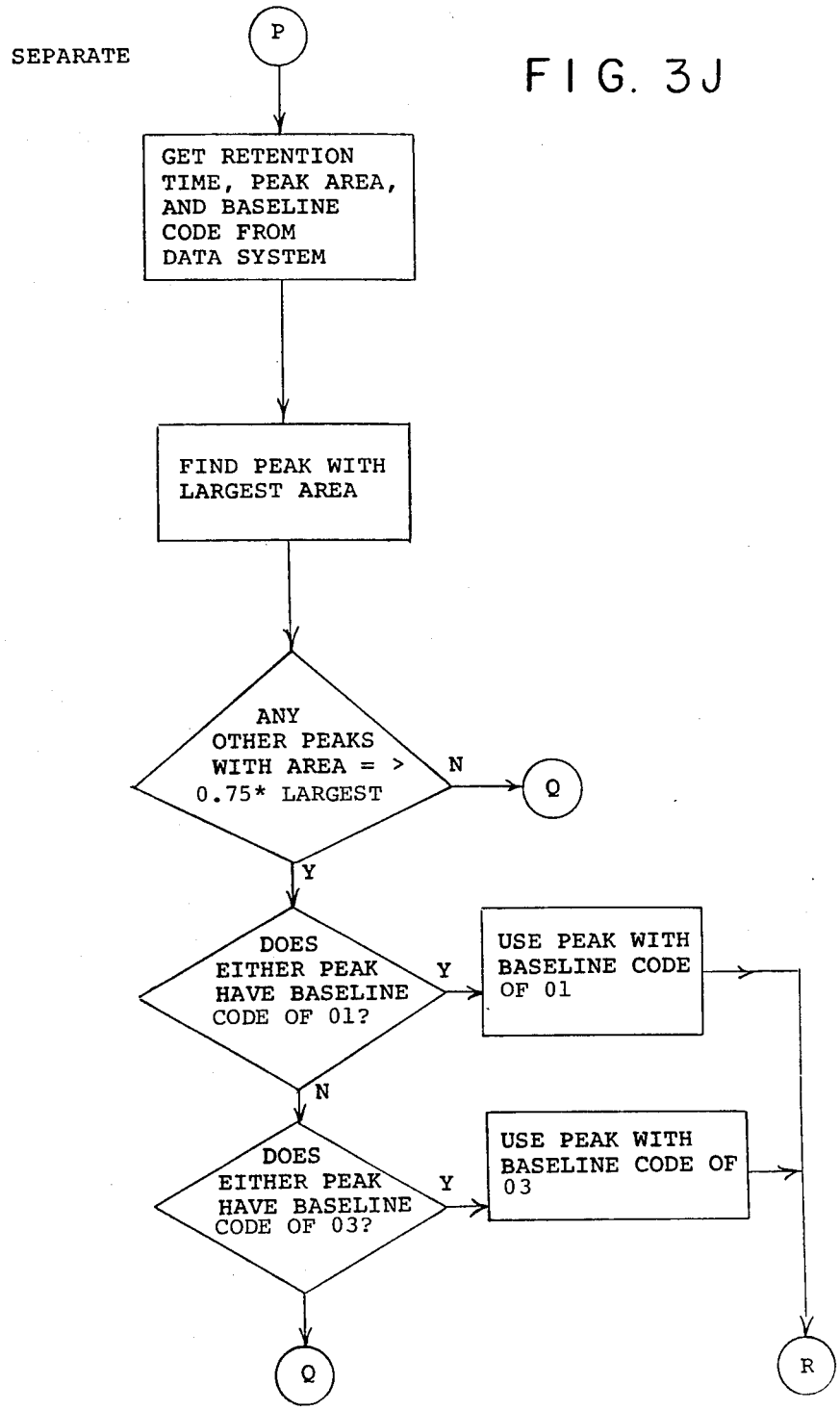

Turning to FIG. 3J, the routine used to identify the major peak is shown. The simplest identification is to use the peak with the largest area. However, in order to eliminate the requirement for pure standards, a secondary selection process is also used. All peak areas received from the data system are examined to see if any have an area greater than 75% of the largest. If not, then the largest area is used. If another peak has an area which qualitifies, the baseline codes are examined. Priority is assigned to a baseline code of 01 which indicates a baseline resolved peak. The second highest priority is assigned to the peak with a code 03, which is the last of a fused group.

Referring to FIG. 3K, if a peak doesn't qualify under one of the above priorities, then the peak with the largest area is used. In either case, the program now discards all information concerning peaks other than the selected peak from the standard vial under test.

This process repeats for each successive standard vial until the total number of standard vials run equals the number of standards the operator said were to be run. At this point, the retention factors k' are computed for all peaks remaining in memory using formula (4) shown above.

Figure 3L:
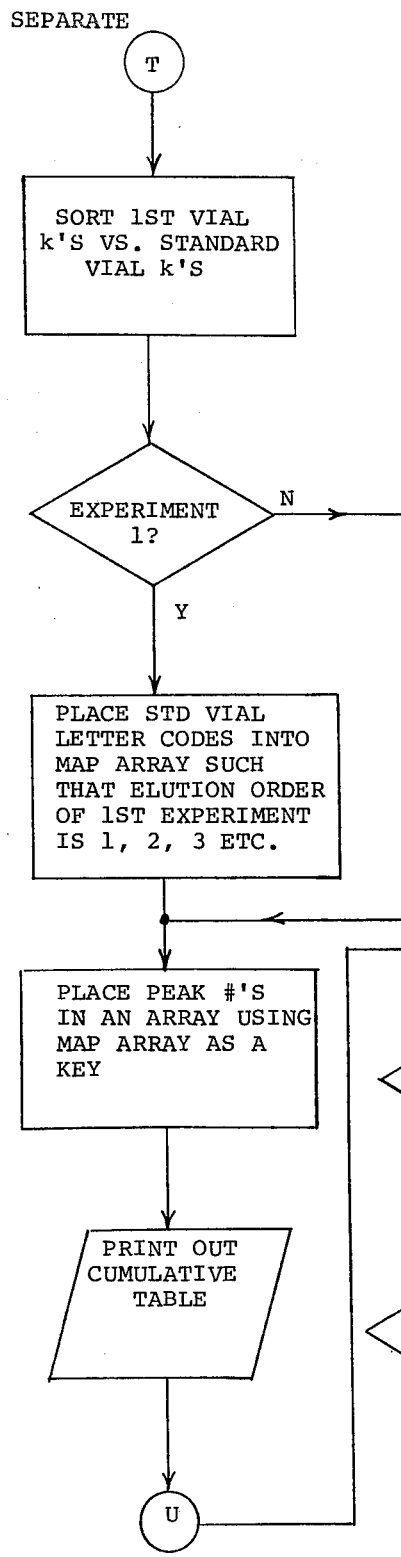
Figure 3M:
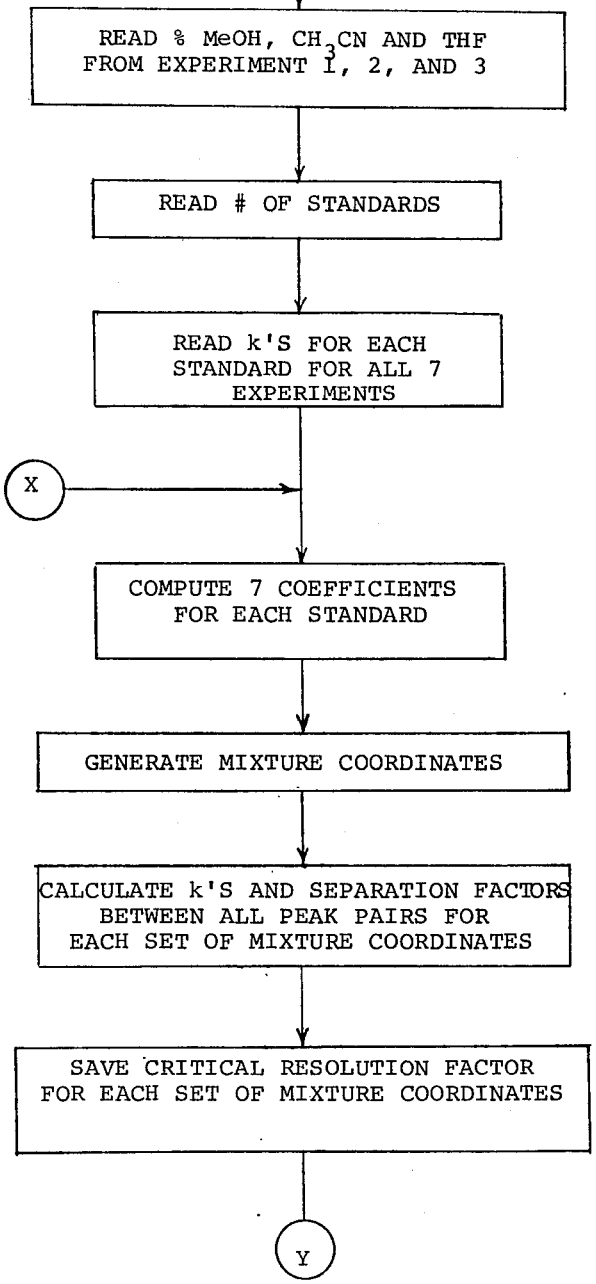

Turning to FIG. 3L, the first operation is to sort the results obtained from the sample vial chromatograph run against the results obtained from the chromatograph runs of the standard vials. To allow for variances in the retention factor k', a sliding scale is used. For k' less than 1, a 15% tolerance is allowed; for k' equal to or greater than 1 but less than 10, 10% is allowed; and for k' greater than or equal to 10, a 5% tolerance is allowed. This routine assigns a mixture peak number to each standards vial.

After the first experiment run on the first or sample vial, a map array is constructed. This array creates a correspondence between the peak elution order in the first experiment and the vial codes. For convention, the vial code is X for the sample vial, which is vial #1 in the autosampler. The following vials, numbered 2 and up, which each contain a single standard solution, each corresponding to one of the different sample components, are coded alphabetically A, B, C, etc. The map array consist of a series of 2 entries, a vial code, and the first experiment elution order number. All further data presentations utilize the first experiment elution number.

The data is now placed in a cumulative array which forms the basis of a printed report. As each experiment is completed, the results are put into the array and the entire contents printed out.

The program now determines if the last experiment run was Experiment 7. If not, the controller places the conditions for the next experiment into the current conditions memory, starts the equilibration timer and repeats all the injections. If the last experiment was number 7, the program ascertains if SOLVE is to be executed. If not the system stops.

SOLVE

If "SOLVE" is to be run, the values of the selectivity solvents methanol, acetonitrile and tetrahydrofuran (in percent) that were used for the first three experiments and the number of standards are read from memory. Next, the retention factor k' for each standard for all experiments is read from memory. Using these data, an ORM map is used to predict and then execute a sample separation using optimum resolution or separating conditions. To accomplish this, as taught by Snee; seven coefficients $\beta$ are calculated for each standard according to the following formulae:

$\beta_1 = k'$ (experiment #1)

$\beta_2 = k'$ (experiment #2)

$\beta_3 = k'$ (experiment #3)

$\beta_4 = 4k'$ (experiment #4)-$2\beta_1$-$2\beta_2$ $\beta_5 = 4k'$ (experiment #5)-$2\beta_2$-$2\beta_3$ $\beta_6 = 4k'$ (experiment #6)-$2\beta_1$-$2\beta_3$ $\beta_7 = 27k'$ (experiment #7)-$9\beta_1$-$9\beta_2$-$9\beta_3$-$3\beta_4$-$3\beta_5$-$3\beta_6$ These coefficients describe the k' behavior of the standard at any blend of the three mobile phases from experiments 1, 2 and 3. The composition of such a blend is defined by three mixture coordinates $X_1$, $X_2$ and $X_3$. The sum of $X_1+X_2+X_3$ is always one. In this system $X_1=0.5$, $X_2=0.3$, $X_3=0.2$ means the blend consists of 50% Experiment 1 mobile phase, 30% Experiment 2 mobile phase, and 20% Experiment 3 mobile phase. The k' of each standard with any specific blend can be determined from the following equation:

$$k' = X_1\beta_1 + X_2\beta_2 + X_3\beta_3 + X_1X_2\beta_4 + X_2X_3\beta_5 + X_1X_3\beta_6 + X_1X_2X_3\beta_7$$

The SOLVE program generates a comprehensive set of mixture coordinates, and for each set of coordinates predicts the k's of all standards. Using this data the separation factor between any two peaks can be calculated as shown below:

$$S=(k'_1-k'_2)/(k'_2+k'_1+2)$$

The separation factor is equal to the resolution divided by one half the square root of the efficiency. The lowest value of the separation factor limits the quality of the chomatography. This value is called the critical resolution factor. For each set of coordinates the critical resolution factor is stored.

The program then evaluates all mixture coordinates to determine the specific coordinates which give the maximum and minimum critical resolution factor. The maximum and minimum values are used to establish a critical resolution range. From this data the computer assigns symbols which correspond to certain fractions of the critical resolution range. A symbol in then assigned to each set of mixture coordinates based on its critical resolution. Then, the "solve" program plots the symbols in an overlapping resolution map and prints the composition required to give the best separation (maximum critical resolution factor) based on the previously stored coordinate and the original percentages of methanol, acetonitrile and tetrahydrofuran. Finally this optimum composition is loaded into the current memory and after equilibration an injection from the first vial is made and the separation completed. The program now stops.

GENERAL

While the method and system example and equation (2), 2(a) in the SCOUT program are based on specific conditions, these equations have relatively broad applicability. Successful extension of the equations used in SCOUT is predicted by theoretical gradient equations such as:

$$tg = \frac{(\Delta t)}{(\Delta \phi)S} \left[ \log \left( 2.3 \frac{(\Delta \phi)F}{(\Delta t)Vm} SK + 1 \right) \right] + \frac{Vm}{F}$$

This equation states that the experimental results will be exactly the same if the ratio of gradient time ($\Delta t$) to composition change ($\Delta \phi$) is held constant and/or if the ratio of column volume (Vm) to flow (F) is constant. This means that there is an infinite number of chromatographic conditions defined by the above restrictions for which the SCOUT equation is strictly applicable.

These equations have been applied on other reversed phase columns, at other temperatures and with acetonitrile instead of methanol as the B solvent. The system has also been used sucessfully where a variety of modifiers have been used in the water reservoir, e.g., acetic acid buffers. In these cases, the program provided very useful predictions. Each of these conditions also implies an infinite set of variations as described by the above equation.

Beyond reversed phase, the equations are untested. It is believed that for normal bonded phase chromatography, there is a reasonable chance of success. In adsorption chromatography, the chances are less due to the differing separation mechanism. However, it probably would be possible to adapt the gradient program to provide a similar change in gradient shape and steepness (change in solvent strength per time) to make the equation equally applicable.

While the SCOUT program has the above noted limitations, the remaining sections not so limited. They may be applied to other temperatures, flow rates, with other columns, different solvents, and even in different modes.

In the event that it is desired to optimize selectivity instead of resolution, the program listing of Appendix I is slightly modified. Specifically, in the SOLVE program, to change from resolution optimization to selectivity optimization, the program is slightly modified. Line 940 is changed to R=A2 and line 950 is changed from IF R<0 then R=−R . . . to IF R<1 then R=1/R.

```
10 COM A1,A9,C1,C4,C7,D2,E1,F1,F6,P1,T1,T3,V1,A5,F7,T2,T4,T5,Z1
20 COM B1(20,20)
30 A1=0 @ A9=0 @ D2=0 @ A5=0
40 E1=0 @ F1=0 @ F6=0 @ F7=0
50 P1=0 @ T1=0 @ T3=0 @ V1=0
60 C1=0 @ C4=0 @ C7=0
70 CLEAR
80 DISP "SELECT FIRST PROGRAM TO BE RUN"
90 ON KEY# 1,"SCOUT" GOTO 170
100 ON KEY# 2,"SEARCH" GOTO 190
110 ON KEY# 3,"%BCD" GOTO 200
120 ON KEY# 4,"SORT " GOTO 210
130 ON KEY# 8,"DOWNLD" GOTO 180
140 ON KEY# 5,"SOLVE" GOTO 220
150 KEY LABEL
160 GOTO 90
170 F6=1 @ GOTO 230
180 CHAIN "DOWNLD"
190 F6=2 @ GOTO 230
200 F6=3 @ GOTO 230
210 F6=4 @ GOTO 230
220 F6=5 @ GOTO 710
230 DISP "SELECT LAST PROGRAM TO BE RUN"
240 ON KEY# 1,"SCOUT" GOTO 310
250 ON KEY# 2,"SEARCH" GOTO 320
260 ON KEY# 3,"%BCD" GOTO 330
270 ON KEY# 4,"SORT " GOTO 340
280 ON KEY# 5,"SOLVE" GOTO 350
290 KEY LABEL
300 GOTO 240
310 F7=1 @ GOTO 360
320 F7=2 @ GOTO 360
330 F7=3 @ GOTO 360
340 F7=4 @ GOTO 360
350 F7=5 @ GOTO 360
360 CLEAR
370 DISP "DESIRED K'";@ INPUT A1
380 DISP "VOID TIME OF COLUMN";@ INPUT T2
390 DISP "MINIMUM AREA";@ INPUT M2
400 OUTPUT 10 ;"MA=";M2
410 DISP "MINIMUM K'";@ INPUT A
420 OUTPUT 10 ;"K1=";A
430 IF F6=1 THEN 470
440 IF F6=2 OR F6=3 THEN 460
450 IF F6=4 THEN 500
460 DISP "INITIAL % B";@ INPUT A5
470 DISP "FLOW RATE";@ INPUT F1
480 DISP "MAXIMUM PRESSURE";@ INPUT P1
490 DISP "OVEN TEMPERATURE";@ INPUT T1
500 DISP "EQUILIBRATION TIME-METHODS" @ INPUT T5
510 DISP "EQUILIBRATION TIME-INJECTIONS" @ INPUT T4
520 IF F6=4 THEN 660
530 DISP "DETECTOR ATTENUATION";
540 INPUT Z1
550 IF Z1=2 THEN Z1=0 @ GOTO 650
560 IF Z1=1 THEN Z1=1 @ GOTO 650
570 IF Z1=.5 THEN Z1=2 @ GOTO 650
580 IF Z1=.2 THEN Z1=3 @ GOTO 650
```

```
590 IF Z1=.1 THEN Z1=4 @ GOTO 650
600 IF Z1=.05 THEN Z1=5 @ GOTO 650
610 IF Z1=.02 THEN Z1=6 @ GOTO 650
620 IF Z1=.01 THEN Z1=7 @ GOTO 650
630 IF Z1=.005 THEN Z1=8 @ GOTO 650
640 IF Z1=.002 THEN Z1=9 @ GOTO 650
650 IF F7<4 THEN 670
660 DISP "# OF VIALS";@ INPUT V1
670 IF F6=1 THEN CHAIN "SCOUT"
680 IF F6=2 THEN CHAIN "SEARCH"
690 IF F6=3 THEN CHAIN "%BCD"
700 IF F6=4 THEN CHAIN "SORT"
710 CHAIN "SOLVE"
 10 CLEAR
 20 COM A1,A9,C1,C4,C7,D2,E1,F1,F6,P1,T1,T3,V1,A5,F7,T2,T4,T5,Z1
 25 COM B1(20,20)
 30 DISP "TRANSFERING PROGRAM"
 40 DIM A$[80],Q$[8000]
 50 SARRAY Q$
 60 ASSIGN# 1 TO "4100"
 70 FOR X=1 TO 31
 80 READ# 1 ; A$
 90 SLET Q$(X) = A$
100 NEXT X
110 ASSIGN# 1 TO *
120 PRINTER IS 10,70
130 FOR X=2 TO 31
140 A$=GET$(Q$(X))
150 PRINT A$;CHR$(13)
160 NEXT X
170 CHAIN "Autost"
1190 !"DUPONT METHOD";Mr,"VIAL #";Vn: GOTO 4495
1200 IF PH<>1 THEN 5210
1210 GOSUB 4450
1220 !"PEAK#";"        HEIGHT";"        AREA";"       RT";
1225 !TAB5"BC";"      N";"      K'";
1230 !TAB6"RS"TAB 13"ALPHA"
1235 T=0: Q=0
1240 FOR N=1 TO Z
1250 Ta=60*PST(N)
1255 Aa(N)=(PST(N)-T3)/T3
1260 Ab(N)=25.13*(((Ta*PSA(N))/PSR(N))**2)
1280 M=N-1: IF M=0 THEN 1320
1285 IF Aa(M)=0 THEN 1300
1290 M=N-1: Af(N)=Aa(N)/Aa(M)
1300 W(N)=(PSR(N)/PSA(N)): W(M)=(PSR(M)/PSA(M))
1305 Tb=60*PST(M)
1310 Ah(N)=(Ta-Tb)/((.44)*(W(N)+W(M)))
1320 !$5NTAB7$9PSA(N)TAB18$9PSR(N)TAB29$5.3PST(N);
1325 !TAB4$2.04PSF(N);
1330 !TAB1$6Ab(N)TAB7$6.3Aa(N)TAB16$6.3Ah(N)TAB25$6.3Af(N)
1340 T=T+PSA(N): Q=Q+PSR(N)
1350 NEXT
1360 !!"TOTALS"TAB8$10TTAB18$10Q
1370 ECHO 1: GOTO 450
4490 IF AN THEN !!"ANALYST": $5.03ANAN(1)AN(2)
4491 GOTO 1190
5200 IF Z<1 THEN !"NO DATA": GO TO 4830
5201 GOTO 1200
 10 SUB "EQUIL2" (T5)
 20 C=T5*60000
 30 ALPHA 1,1
 40 CLEAR
 50 DISP "   TIME UNTIL NEXT INJECTION"
 60 ALPHA 2,12
 70 ON TIMER# 1,C GOTO 150
 80 A=READTIM(1)
 90 A=INT(A)
100 B=T5*60-A
110 DISP HMS$(B)
120 ALPHA 2,12
130 WAIT 1000
```

```
140 GOTO 80
150 OUTPUT 10 ;"TFN";CHR$(34);"T31";CHR$(34);"TFN";CHR$(34);"T30";CHR$(34)
160 OFF TIMER# 1
170 OFF CURSOR
180 CLEAR
190 SUBEND
 10 COM A1,A9,C1,C4,C7,D2,E1,F1,F6,P1,T1,T3,V1,A5,F7,T2,T4,T5,Z1
 20 COM B1(20,20)
 30 CLEAR
 40 DIM A$[70],B$[70],C$[70],D$[70],E$[70],F$[70],G$[70],H$[70],I$[70]
 50 OUTPUT 5 ;"SE"
 60 OUTPUT 5 ;"LD";9
 70 OUTPUT 5 ;"SA"
 80 OUTPUT 5 ;"FC=";0
 90 OUTPUT 5 ;"SB"
100 OUTPUT 5 ;"FC=";100
110 OUTPUT 5 ;"SL=";20
120 OUTPUT 5 ;"IC(=";100
130 OUTPUT 5 ;"FC=";100
140 OUTPUT 5 ;"SA"
150 OUTPUT 5 ;"IC=";0
160 OUTPUT 5 ;"FC=";0
170 OUTPUT 5 ;"SL=";10
180 OUTPUT 5 ;"FL=3"
190 OUTPUT 5 ;"PU=";P1
200 OUTPUT 5 ;"TC=";T1
210 OUTPUT 5 ;"A1=";RPT$(CHR$(188),9)
220 OUTPUT 5 ;"A1=";RPT$(CHR$(190),Z1)
230 OUTPUT 5 ;"HM"
240 OUTPUT 5 ;"RE"
250 OUTPUT 5 ;"SV";1
260 OUTPUT 5 ;"ON"
270 FOR N=1 TO 200 @ NEXT N
280 OUTPUT 5 ;"SV";0
290 IMAGE #,2X,K
300 IMAGE #,6X,K
310 IMAGE #,8X,K
320 ENTER 5 USING 290 ; A$
330 ENTER 5 USING 300 ; B$,C$,D$
340 ENTER 5 USING 310 ; E$,F$,G$,H$,I$
350 IMAGE #,K
360 OUTPUT 10 ;"",CHR$(13)
370 OUTPUT 10 USING 350 ; A$,CHR$(13),B$,CHR$(13),C$,CHR$(13)
380 OUTPUT 10 USING 350 ; D$,CHR$(13),E$,CHR$(13),F$,CHR$(13)
390 OUTPUT 10 USING 350 ; G$,CHR$(13),H$,CHR$(13),I$,CHR$(13)
400 OUTPUT 10 ;CHR$(14)
410 FOR N=450 TO 780 STEP 10
420 OUTPUT 10 ;N
430 NEXT N
440 OUTPUT 10 ;"TT(6)=30"
450 OUTPUT 10 ;"TF(6)=";CHR$(34);"ER0";CHR$(34)
460 OUTPUT 10 ;"TFN";CHR$(34);"T61";CHR$(34)
470 OUTPUT 10 ;"450 FOR A=1 TO Z:"
480 OUTPUT 10 ;"460 IF Aa(A))=1 THEN 480:"
490 OUTPUT 10 ;"470 NEXT A:"
500 OUTPUT 10 ;"480 N=Z:"
510 OUTPUT 10 ;"490 IF PSF(N))10 THEN N=Z-1:"
520 OUTPUT 10 ;"500 POKE#8C107,8:DV=2:POKE#C388,PEEK#C387:"
530 OUTPUT 10 ;"510 !PST(N):"
540 OUTPUT 10 ;"520 ! PST(A):"
550 OUTPUT 10 ;"530 DV=1:POKE#8C107,0:"
560 OUTPUT 10 ;"540 GOTO 4840:"
570 CLEAR
580 DISP "WAITING FOR DATA"
590 CONTROL 10,9 ; 4
600 CONTROL 10,9 ; 137
610 CONTROL 10,1 ; 16
620 ON INTR 10 GOTO 640
630 GOTO 620
640 ENTER 10 ; B1
650 ENTER 10 ; D1
```

```
660 A=.00233 @ B=-.06118 @ C=.63021 @ D=-.57685 @ E=-.01613 @ F=-.00702
670 L1=A*B1^3+B*B1^2+C*B1+D
680 L2=A*D1^3+B*D1^2+C*D1+D
690 DISP "Log K'=";L1
700 D2=E+F*L1
710 D3=E+F*L2
720 DISP "CALCUATED SLOPE IS";D2
730 E1=INT((LGT(A1)-L1)/D2)
740 A2=D3*E1+L2
750 A=LGT(A1)-A2
760 D1=D1^A
770 DISP "TO OBTAIN K'=";A1;"USE";E1;"% METHANOL"
780 DISP "RANGE OF K' IS";D1
790 COPY
800 IF F7>1 THEN CHAIN "SEARCH"
810 DISP "DO YOU WISH TO RUN AGAIN ...YES(1) OR NO(0)?";
820 INPUT Z
830 IF Z=1 THEN 570
840 CHAIN "Autost"
 10 COM A1,A9,C1,C4,C7,D2,E1,F1,F6,P1,T1,T3,V1,A5,F7,T2,T4,T5,Z1
 15 COM B1(20,20)
 20 CLEAR
 30 DISP "RUNNING"
 40 DIM A(20,3),A$[70],B$[70],C$[70],D$[70],E$[70],F$[70],G$[70],H$[70],I$[70]
 50 R1=0 @ R2=0 @ A2=0 @ A3=0 @ A4=0 @ A6=0 @ A7=0 @ A8=0 @ C2=0 @ C3=0
 60 C5=0 @ C6=0 @ C8=0 @ C9=0 @ F3=0 @ F4=0
 70 FOR N=450 TO 700 STEP 10
 80 OUTPUT 10 ;N
 90 NEXT N
100 OUTPUT 10 ;"450 POKE#8C107,8:DV=2:POKE#C388,PEEK#C387"
110 OUTPUT 10 ;"460    ! Aa(Z):"
120 OUTPUT 10 ;"470 DV=1:POKE#8C107,0"
130 OUTPUT 10 ;"480 GOTO 4840"
140 A=A1*T2+(T2+5)
150 OUTPUT 10 ;"TT(6)=";A
160 OUTPUT 10 ;"TF(6)=";CHR$(34);"ER0";CHR$(34)
170 IF F6=1 THEN GOTO 1230 ELSE 1100
180 DISP "WAITING FOR DATA"
190 CONTROL 10,9 ; 4
200 CONTROL 10,9 ; 137
210 CONTROL 10,1 ; 16
220 ON INTR 10 GOTO 240
230 GOTO 220
240 ENTER 10 ; A9
250 DISP "K'=";A9
260 R1=R1+1
270 R2=R2+1
280 A(R2,1)=R1
290 A(R2,2)=A9
300 A(R2,3)=B3
310 F5=0 @ F2=0 @ IF A9>=.9*A1 THEN F5=1
320 IF A9<=1.1*A1 THEN F2=1
330 IF F5 AND F2 THEN A8=A8+1
340 IF F5 AND F2 THEN 440
350 IF R1=1 THEN 370
360 A3=(L1-LGT(A9))/(A2-B3)
370 A2=B3
380 L1=LGT(A9)
390 IF R1=1 THEN 400 ELSE 410
400 A3=(L1+2.297)/(B3-142.45)
410 L2=L1-A2*A3 @ L3=LGT(A1)
420 B3=INT((L3-L2)/A3)
430 IF B3>100 THEN B3=100
435 IF B3<0 THEN B3=0
437 IF B3=A2 THEN 1250
440 IF A8=1 AND F3=0 THEN 870
450 IF A8=2 AND F4=0 THEN 890
460 IF A8=3 THEN 910
470 IF A8=0 THEN A5=B3 @ A4=100-A5
480 IF A8=1 THEN A6=B3 @ A4=100-A6
490 IF A8=2 THEN A7=B3 @ A4=100-A7
500 CLEAR
```

```
510 DISP "NEXT...SLOPE=";A3
520 DISP "%A= ";A4
530 DISP "%B= ";A5
540 DISP "%C= ";A6
550 DISP "%D= ";A7
560 COPY
570 OUTPUT 5 ;"SE"
580 OUTPUT 5 ;"RT"
590 OUTPUT 5 ;"SL=";0
600 OUTPUT 5 ;"SA"
610 OUTPUT 5 ,"IC=",A4
620 OUTPUT 5 ;"FC=",A4
630 OUTPUT 5 ;"SB"
640 OUTPUT 5 ;"IC=";A5
650 OUTPUT 5 ;"FC=";A5
660 OUTPUT 5 ;"SC"
670 OUTPUT 5 ;"IC=";A6
680 OUTPUT 5 ;"FC=";A6
690 OUTPUT 5 ;"SD"
700 OUTPUT 5 ;"IC=";A7
710 OUTPUT 5 ;"FC=";A7
720 OUTPUT 5 ;"SV0"
730 IMAGE #,2X,K
740 IMAGE #,6X,K
750 IMAGE #,8X,K
760 ENTER 5 USING 730 ; A$
770 ENTER 5 USING 740 ; B$,C$,D$
780 ENTER 5 USING 750 ; E$,F$,G$,H$,I$
790 IMAGE #,K
800 OUTPUT 10 ;"",CHR$(13)
810 OUTPUT 10 USING 790 ; A$,CHR$(13),B$,CHR$(13)
820 OUTPUT 10 USING 790 ; D$,CHR$(13)
830 OUTPUT 10 USING 790 ; H$,CHR$(13),I$,CHR$(13)
840 OUTPUT 10 ;CHR$(14)
850 CALL "EQUIL2" ( TS )
860 GOTO 180
870 C1=A5 @ C2=A3 @ C3=A4 @ A5=0 @ A6=INT(C1*2.67/3.14)
880 F3=1 @ A4=100-A6 @ R1=0 @ A2=A6 @ B3=A6 @ GOTO 500
890 C4=A6 @ C5=A3 @ C6=A4 @ A6=0 @ A7=INT(C1*2.67/4.4)
900 A4=100-A7 @ R1=0 @ F4=1 @ A2=A7 @ B3=A7 @ GOTO 500
910 C7=A7 @ C8=A3 @ C9=A4
920 CLEAR
930 DISP "OPTIMUM % ORGANIC FOR K' OF ";A1
940 DISP "SOLVENT";"   %A";"   % ORGANIC";"   SLOPE"
950 IMAGE K,3X,K,7X,K,5X,K
960 DISP USING 950 ; "MEOH    ",C3,C1,C2
970 DISP USING 950 ; "ACN     ",C6,C4,C5
980 DISP USING 950 ; "THF     ",C9,C7,C8
990 COPY
1000 CLEAR
1010 IF F7>2 THEN CHAIN "%BCD"
1020 DISP "DO YOU WANT TO RUN AGAIN(Y OR N)?"
1030 BEEP 50,500
1040 BEEP 100,500
1050 ON TIMER# 1,5000 GOTO 1000
1060 INPUT A$
1070 OFF TIMER# 1
1080 IF A$="Y" THEN 1100
1090 GOTO 1280
1100 B1=-.026 @ B2=A5 @ A3=B1 @ B3=A5
1110 CLEAR
1120 OUTPUT 5 ;"LD";9
1130 WAIT 2000
1140 OUTPUT 5 ;"A1=";RPT$(CHR$(188),9)
1150 OUTPUT 5 ;"A1=";RPT$(CHR$(190),Z1)
1160 OUTPUT 5 ;"FL=";F1
1170 OUTPUT 5 ;"PU=";P1
1180 OUTPUT 5 ;"TC=";T1
1190 OUTPUT 5 ;"RE"
1200 OUTPUT 5 ;"ON"
1210 A4=100-A5 @ A2=A5
1220 GOTO 500
```

```
1230 B3=E1 @ A5=E1 @ A3=D2 @ B1=D2 @ B2=E1 @ A2=E1 @ A4=100-A5
1240 B3=A5 @ GOTO 1110
1250 DISP "DESIRED K' CANNOT BE OBTAINED.DO YOU WISH TO CHANGE DESIRED K'(Y OR N
)?"
1260 INPUT A$
1270 IF A$="Y" THEN 1100
1280 CHAIN "Autost"

10 COM A1,A9,C1,C4,C7,D2,E1,F1,F6,P1,T1,T3,V1,A5,F7,T2,T4,T5,Z1
 20 COM B1(20,20)
 30 DIM A$[70],B$[70],C$[70],D$[70],E$[70],F$[70],G$[70],H$[70],I$[70]
 40 FOR A=1 TO 7
 50 A(A)=0 @ B(A)=0 @ C(A)=0 @ D(A)=0
 60 NEXT A
 70 CLEAR
 80 IF F6=3 THEN B(1)=A5 @ GOTO 120
 90 IF C1<>0 THEN 110
100 DISP "INITIAL % MEOH?" @ INPUT B(1)@ GOTO 120
110 B(1)=C1 @ C(2)=C4 @ D(3)=C7 @ GOTO 130
120 C(2)=INT(B(1)*2.67/3.14) @ D(3)=INT(B(1)*2.67/4.4)
130 B(4)=INT(B(1)/2) @ B(6)=B(4) @ C(4)=INT(C(2)/2) @ C(5)=C(4) @ D(5)=INT(D(3)/
2) @ D(6)=D(5)
140 B(7)=INT(B(1)/3) @ C(7)=INT(C(2)/3)
150 D(7)=INT(D(3)/3) @ A(1)=100-B(1) @ A(2)=100-C(2) @ A(3)=100-D(3) @ A(4)=100-
(B(4)+C(4))
160 A(5)=100-(C(5)+D(5)) @ A(6)=100-(B(6)+D(6)) @ A(7)=100-(B(7)+C(7)+D(7))
170 CLEAR
180 IMAGE K,4X,K,2X,K,2X,K,2X,K
190 IMAGE 10X,K,X,K,5X,K,5X,K,4X,K
200 DISP "EQUAL SOLVENT STRENGTH FOR";B(1);"% METHANOL"
210 DISP USING 190 ; " ";"%";"%";"%";"%"
220 DISP USING 180 ; "METHOD";"WATER";"MEOH";"ACN";"THF "
230 FOR N=1 TO 7
240 DISP TAB(3);N;TAB(12);A(N);TAB(18);B(N);TAB(24);C(N);TAB(29);D(N)
245 C1=B(1) @ C4=C(2) @ C7=D(3)
250 NEXT N
260 IF F6<>3 THEN 360
270 DISP "ARE THESE VALUES OK?"
280 INPUT J$
290 IF J$="Y" THEN 360
300 DISP "WHICH DO YOU WISH TO CHANGE:% ACN(1)% THF(2) OR BOTH(3)?"
310 INPUT B1
320 ON B1 GOTO 330,340,330
330 DISP "DESIRED % ACN?" @ INPUT C(2)@ IF B1=1 THEN 130
340 DISP "DESIRED % THF?" @ INPUT D(3)@ GOTO 130
350 END
360 OUTPUT 5 ;"SE"
370 OUTPUT 5 ;"LD";9
380 WAIT 2000
390 OUTPUT 5 ;"RT"
400 OUTPUT 5 ;"RE"
410 OUTPUT 5 ;"A1=";RPT$(CHR$(188),1)
420 OUTPUT 5 ;"A1=";RPT$(CHR$(190),Z1)
430 OUTPUT 5 ;"FL=";F1
440 OUTPUT 5 ;"PU=";P1
450 OUTPUT 5 ;"TC=";T1
460 FOR B=1 TO 7
470 OUTPUT 5 ;"SA"
480 OUTPUT 5 ;"IC=";A(B)
490 OUTPUT 5 ;"FC=";A(B)
500 OUTPUT 5 ;"SB"
510 OUTPUT 5 ;"IC=";B(B)
520 OUTPUT 5 ;"FC=";B(B)
530 OUTPUT 5 ;"SC"
540 OUTPUT 5 ;"IC=";C(B)
550 OUTPUT 5 ;"FC=";C(B)
560 OUTPUT 5 ;"SD"
570 OUTPUT 5 ;"IC=";D(B)
580 OUTPUT 5 ;"FC=";D(B)
590 OUTPUT 5 ;"SV";B
600 NEXT B
```

```
610 OUTPUT 5 ;"LD";1
620 WAIT 2000
630 OUTPUT 5 ;"ON"
640 WAIT 2000
650 OUTPUT 5 ;"SE"
660 OUTPUT 5 ;"SV0"
670 IMAGE #,2X,K
680 IMAGE #,6X,K
690 IMAGE #,8X,K
700 ENTER 5 USING 670 ; A$
710 ENTER 5 USING 680 ; B$,C$,D$
720 ENTER 5 USING 690 ; E$,F$,G$,H$,I$
730 WAIT 2000
740 OUTPUT 5 ;"M?"
750 ENTER 5 ; M
760 IMAGE #,K
770 OUTPUT 10 ;"",CHR$(13)
780 OUTPUT 10 ;"DUPONT METHOD #";CHR$(M+48)
790 OUTPUT 10 USING 760 ; B$,CHR$(13)
800 OUTPUT 10 USING 760 ; D$,CHR$(13)
810 OUTPUT 10 USING 760 ; H$,CHR$(13),I$,CHR$(13)
820 OUTPUT 10 ;CHR$(14)
830 IF F7>3 THEN 840 ELSE 860
840 CALL "EQUIL2" ( T5 )
850 CHAIN "SORT"
860 CHAIN "Autost"

10 COM A1,A9,C1,C4,C7,D2,E1,F1,F6,P1,T1,T3,V1,A5,F7,T2,T4,T5,Z1
15 COM B1(20,20)
20 CLEAR
30 DISP "RUNNING"
40 DIM A$[70],B$[70],C$[70],D$[70],E$[70],F$[70],G$[70]
50 SHORT A(20,20),A2(20,2),A3(20,20),A4(20,7),Z(20),A5(20,7),T(20),A6(20,7)
60 DIM H$[70],I$[70]
70 MAT A=ZER
80 MAT Z=ZER
90 MAT B1=ZER
91 MAT A2=ZER
92 MAT A3=ZER
93 MAT A4=ZER
94 MAT A5=ZER
95 MAT T=ZER
96 MAT A6=ZER

250 Z=0 @ T(0)=0 @ X1=0
260 T1=INT(1.5*(A1*T2)+.9)
270 OUTPUT 10 ;"TT(6)=";T1
280 OUTPUT 10 ;"TF(6)=";CHR$(34);"ER0";CHR$(34)
290 OUTPUT 10 ;"RN=0:Vn=1:Mr=1:T3=";T2
300 FOR N=450 TO 780 STEP 10
310 OUTPUT 10 ;N
320 NEXT N
330 OUTPUT 10 ;"450 A=0:B=0:C=0:D=0:E=0:F=0:"
340 OUTPUT 10 ;"460 FOR N=1 TO Z "
350 OUTPUT 10 ;"470 IF Aa(N)> K1 THEN A=A+1:"
360 OUTPUT 10 ;"480 IF B=0 THEN 490 ELSE 500:"
370 OUTPUT 10 ;"490 IF Aa(N)> K1 THEN B=N:"
380 OUTPUT 10 ;"500 NEXT N:"
390 OUTPUT 10 ;"510 IF Vn=1 THEN 660:"
400 OUTPUT 10 ;"520 FOR N=B TO (A+B)-1:"
410 OUTPUT 10 ;"530 IF PSR(N)>C THEN C=PSR(N):"
420 OUTPUT 10 ;"540 IF PSR(N)=C THEN D=N:"
430 OUTPUT 10 ;"550 NEXT:"
440 OUTPUT 10 ;"560 IF A=1 THEN 660:"
450 OUTPUT 10 ;"570 FOR N=B TO ((A+B)-1):"
460 OUTPUT 10 ;"580 IF D=N THEN 640:"
470 OUTPUT 10 ;"590 IF PSR(N)>.75*PSR(D) THEN E=N:"
480 OUTPUT 10 ;"600 IF PSF(D)=1  THEN F=D:GOTO 650:"
490 OUTPUT 10 ;"610 IF PSF(E)=1 THEN F=E:GOTO 650:"
500 OUTPUT 10 ;"620 IF PSF(E)>=PSF(D) THEN F=E:"
510 OUTPUT 10 ;"630 IF PSF(D)> PSF(E) THEN F=D:"
```

```
520 OUTPUT 10 ;"640 NEXT:"
530 OUTPUT 10 ;"650 B=F:A=1:"
540 OUTPUT 10 ;"660 POKE#8C107,8:DV=2:POKE#C388,PEEK#C387:"
550 OUTPUT 10 ;"670 !Vn:"
560 OUTPUT 10 ;"680 ! A:"
570 OUTPUT 10 ;"690 FOR N=B TO((A+B)-1):"
580 OUTPUT 10 ;"700 IF A=0 THEN 730:"
590 OUTPUT 10 ;"710 ! $6.3 Aa(N):"
600 OUTPUT 10 ;"720 NEXT N:"
610 OUTPUT 10 ;"730 !Mr:"
620 OUTPUT 10 ;"740 DV=1:POKE#8C107,0:"
630 OUTPUT 10 ;"TFN";CHR$(34);"T31";CHR$(34);"TFN";CHR$(34);"T30",CHR$(34)
640 OUTPUT 10 ;" 750 Vn=Vn+1"
650 OUTPUT 10 ;" 760 GOTO 4840:"
660 OUTPUT 10 ;"TFN";CHR$(34);"T60";CHR$(34)
670 CONTROL 10,9 ; 4
680 CLEAR
690 DISP "WAITING FOR DATA"
700 CONTROL 10,9 ; 137
710 CONTROL 10,1 ; 16
720 ON INTR 10 GOTO 740
730 GOTO 720
740 ENTER 10 ; V
750 DISP "VIAL#";V
760 ENTER 10 ; Y
770 DISP "# OF PEAKS=";Y
780 IF Y>Z THEN Z=Y
790 IF Y=0 THEN 850
800 FOR N=1 TO Y
810 ENTER 10 ; C
820 A(V,N)=C
830 DISP "K'=";C
840 NEXT N
850 ENTER 10 ; M1
860 DISP "METHOD #";M1
870 A(V,0)=M1
880 COPY
890 IF V1=V THEN GOTO 930
900 CALL "EQUIL2" ( T4 )
910 GOTO 670
920 CLEAR
930 FOR N=2 TO V1
940 B1(M1,N-1)=A(N,1)
941 NEXT N
960 FOR W=1 TO Z
970 FOR N=2 TO V1
990 C=A(1,W)
1000 IF C=0 THEN 1120
1010 IF C<=1 THEN 1020 ELSE 1030
1020 E=.85 @ F=1.15 @ GOTO 1070
1030 IF C>1 AND C<=10 THEN 1040 ELSE 1050
1040 E=.9 @ F=1.1 @ GOTO 1070
1050 IF C>10 THEN 1060
1060 E=.95 @ F=1.05
1070 G=E*C @ H=F*C
1080 IF A(N,1)>=G AND A(N,1)<=H THEN 1090 ELSE 1120
1090 A3(N,1)=W
1100 A(N,1)=0
1120 NEXT N
1130 NEXT W
1140 IF A(1,0)=1 THEN 1160
1150 GOTO 1290
1160 Y=65
1170 FOR N=2 TO V1
1180 Z(N)=Y
1190 Y=Y+1
1200 NEXT N
1210 FOR Y=1 TO Z
1230 FOR W=2 TO V1
1240 IF A3(W,1)=Y THEN A2(Y,1)=Z(W) ELSE 1260
1250 A2(Y,2)=W
1260 NEXT W
```

```
1280 NEXT Y
1290 FOR N=1 TO Z
1300 A4(N,M1)=A3(A2(N,2),1)
1310 NEXT N
1320 FOR N=1 TO V1-1
1330 T(N)=A3(N+1,1)
1340 NEXT N
1350 FOR N=1 TO V1-2
1360 FOR Y=N+1 TO V1-1
1370 IF T(N)=0 THEN 1430
1380 IF T(N)<=T(Y) THEN 1420
1390 R=T(N)
1400 T(N)=T(Y)
1410 T(Y)=R
1420 NEXT Y
1430 NEXT N
1440 A2=0
1450 FOR N=1 TO V1-1
1470 FOR Y=2 TO V1
1480 IF T(N)=0 THEN A2=A2+1
1490 IF T(N)=0 THEN 1570
1500 IF T(N)=T(N-1) THEN 1570
1510 IF T(N)=A3(Y,1) THEN 1520 ELSE 1560
1520 FOR W=1 TO V1-1
1530 IF A2(W,1)=Y+63 THEN 1550
1540 NEXT W
1550 A5(W,M1)=N-A2+48
1560 NEXT Y
1570 NEXT N
1580 FOR W=1 TO V1-1
1590 IF A5(W,M1)=32 THEN A5(W,M1)=88
1600 NEXT W
1610 C=A(1,0)
1620 CLEAR
1630 PRINT "PEAK ELUTION ORDER"
1640 PRINT TAB(1);"METHOD   ";TAB(13);"METHOD"
1650 PRINT TAB(4);"#1";TAB(15);"#";A(1,0);TAB(21);"MIXTURE"
1660 PRINT "PEAK#/VIAL";TAB(13);"PEAKS";TAB(20);"PEAK#";TAB(28);"K'"
1680 FOR N=1 TO Z
1690 S(1)=A4(N,M1)+48
1700 A4(N,M1)=S(1)
1710 IF A2(N,1)=32 THEN S7=32 ELSE S7=N+48
1720 C=A(1,0)
1730 PRINT TAB(3);CHR$(S7);TAB(6);"/";TAB(8);CHR$(A2(N,1));
1740 PRINT TAB(15);CHR$(A4(N,M1));
1750 PRINT TAB(21);N;TAB(26);A(1,N)
1760 NEXT N
1770 PRINT @ PRINT @ PRINT
1780 MAT A=ZER
1790 MAT A3=ZER
1840 GOTO 1860
1850 GOTO 670
1860 CLEAR
1870 OUTPUT 5 ;"SE"
1880 M1=M1+1
1890 OUTPUT 5 ;"LD";M1
1900 FOR N=1 TO 500 @ NEXT N
1910 OUTPUT 5 ;"ON"
1920 FOR N=1 TO 250 @ NEXT N
1930 GOTO 2130
1940 OUTPUT 5 ;"M?"
1950 ENTER 5 ; M1
1960 OUTPUT 5 ;"SV0"
1970 IMAGE #,2X,K
1980 IMAGE #,6X,K
1990 IMAGE #,8X,K
2000 ENTER 5 USING 1970 ; A$
2010 ENTER 5 USING 1980 ; B$,C$,D$
2020 ENTER 5 USING 1990 ; E$,F$,G$,H$,I$
2030 IMAGE #,K
2040 OUTPUT 10 ;"",CHR$(13)
2050 OUTPUT 10 ;"DUPONT METHOD   #";CHR$(M1+48)
```

```
2060 OUTPUT 10 USING 2030 ; B$,CHR$(13)
2070 OUTPUT 10 USING 2030 ; D$,CHR$(13)
2080 OUTPUT 10 USING 2030 ; H$,CHR$(13),I$,CHR$(13)
2090 OUTPUT 10 ;CHR$(14)
2100 OUTPUT 10 ;"Vn=1:Mr=";M1
2110 CALL "EQUIL2" ( T5 )
2120 GOTO 670
2130 OUTPUT 10 ;""
2140 PRINTER IS 10,70
2150 IMAGE 38X,K
2160 IMAGE K,5X,K,8X,K,8X,K,8X,K,8X,K,8X,K,8X,K
2170 PRINT USING 2150 ; "METHOD#"
2180 PRINT USING 2160 ; "COMPOUND";1;2;3;4;5;6;7
2190 OUTPUT 10 ;CHR$(13)
2200 IMAGE #,2X,K,5X,"I"
2210 IMAGE #,4X,K,3X,"I"
2220 IMAGE 3X,K,3X,"I"
2230 FOR N=1 TO Z
2240 PRINT USING 2200 ; CHR$(A2(N,1))
2250 PRINT USING 2210 ; CHR$(A5(N,1));CHR$(A5(N,2));CHR$(A5(N,3));CHR$(A5(N,4))
2260 PRINT USING 2210 ; CHR$(A5(N,5));CHR$(A5(N,6))
2270 PRINT USING 2220 ; CHR$(A5(N,7))
2280 NEXT N
2290 OUTPUT 10 ;CHR$(14)
2300 PRINTER IS 2
2310 IF M1=8 THEN 2340 ELSE 2330
2320 IF X1=1 THEN 2340
2330 GOTO 1960
2340 OUTPUT 10 ;"TFN";CHR$(34);"T31";CHR$(34)
2350 OUTPUT 5 ;"OF"
2360 CLEAR
2370 DISP "RUN IS NOW COMPLETE"
2380 DISP "ARE THE RESULTS SATISFACTORY?"
2390 DISP "YES(Y) OR NO(N)?"
2400 INPUT J$
2410 IF J$="N" THEN 2430
2420 IF J$="Y" THEN 2425 ELSE GOTO 2380
2425 IF F7=5 THEN CHAIN "SOLVE"
2426 CHAIN "Autost"
2430 DISP "WHICH METHOD IS TO BE REPEATED";@ INPUT M1
2440 OUTPUT 5 ;"LD";M1
2450 FOR N=1 TO 200 @ NEXT N
2460 OUTPUT 5 ;"ON"
2470 FOR N=1 TO 200 @ NEXT N
2480 CALL "EQUIL2" ( T5 )
2490 OUTPUT 10 ;"TFN";CHR$(34);"T30";CHR$(34)
2500 OUTPUT 10 ;"Mr=";M1
2510 OUTPUT 10 ;"Vn=1"
2520 X1=1
2530 GOTO 680
  10 CLEAR
  20 COM A1,A9,C1,C4,C7,D2,E1
  30 COM F1,F6,P1,T1,T3,V1,A5
  40 COM F7,T2,T4,T5,Z1,B1(20,20)
  50 DIM Z$[70],A$[3000]
  60 SHORT B(35,70)
  70 MAT B=ZER
  80 IF F6=5 THEN 90 ELSE 350
  90 MAT B1=ZER
 100 DISP "INPUT # OF COMPOUNDS";
 110 INPUT V1
 120 V1=V1+1
 130 DISP "INPUT % MEOH";
 140 INPUT C1
 150 DISP "INPUT % CH3CN";
 160 INPUT C4
 170 DISP "INPUT % THF";
 180 INPUT C7
 182 DISP "INPUT k'(1) OR RT(2) ?"
 183 INPUT Q
 184 IF Q=1 THEN 200
```

```
185 DISP "INPUT to"
186 INPUT T0
190 FOR N=1 TO V1-1
200 DISP "METHOD#1 RESULT";
210 INPUT B1(1,N)
215 IF Q=2 THEN B1(1,N)=-1+B1(1,N)/T0
217 PRINT "K(1) = ";B1(1,N)
220 DISP "METHOD#2 RESULT";
230 INPUT B1(2,N)
235 IF Q=2 THEN B1(2,N)=-1+B1(2,N)/T0
237 PRINT "K(2) = ";B1(2,N)
240 DISP "METHOD#3 RESULT";
250 INPUT B1(3,N)
255 IF Q=2 THEN B1(3,N)=-1+B1(3,N)/T0
257 PRINT "K(3) = ";B1(3,N)
260 DISP "METHOD#4 RESULT";
270 INPUT B1(4,N)
275 IF Q=2 THEN B1(4,N)=-1+B1(4,N)/T0
277 PRINT "K(4) = ";B1(4,N)
280 DISP "METHOD#5 RESULT";
290 INPUT B1(5,N)
295 IF Q=2 THEN B1(5,N)=-1+B1(5,N)/T0
297 PRINT "K(5) = ";B1(5,N)
300 DISP "METHOD#6 RESULT";
310 INPUT B1(6,N)
315 IF Q=2 THEN B1(6,N)=-1+B1(6,N)/T0
317 PRINT "K(6) = ";B1(6,N)
320 DISP "METHOD#7 RESULT";
330 INPUT B1(7,N)
335 IF Q=2 THEN B1(7,N)=-1+B1(7,N)/T0
337 PRINT "K(7) = ";B1(7,N)
339 PRINT
340 NEXT N
350 SARRAY A$
360 Z$[1]=CHR$(175)
370 Z$[69]=CHR$(220)
380 B$="-"
390 Z$[1,70]=RPT$(B$,69)
400 A=49
410 FOR N=11 TO 61 STEP 10
420 Z$[N,N]=CHR$(124)
430 A=A+1
440 NEXT N
450 SLET A$(35) = Z$
460 Z$=" "
470 Z$=RPT$(Z$,70)
480 A=35
490 FOR N=1 TO 34
500 IF N=10 THEN Z$[23,24]="10" @ Z$[46,47]="10" @ GOTO 530
510 IF N=20 THEN Z$[13,14]="20" @ Z$[56,57]="20" @ GOTO 530
520 IF N=30 THEN Z$[3,4]="30" @ Z$[66,67]="30"
530 Z$[A-N,A-N]="/"
540 SLET A$(N) = Z$
550 Z$=" "
560 Z$=RPT$(Z$,70)
570 NEXT N
580 FOR N=1 TO V1-1
590 A=B1(1,N) @ D=B1(2,N) @ C=B1(3,N)
600 B1(4,N)=4*B1(4,N)-2*A-2*D
610 B1(5,N)=4*B1(5,N)-2*D-2*C
620 B1(6,N)=4*B1(6,N)-2*A-2*C
630 B1(7,N)=27*B1(7,N)-9*A-9*D-9*C-3*B1(4,N)-3*B1(5,N)-3*B1(6,N)
640 NEXT N
650 FOR N=1 TO V1-1
660 PRINT N,B1(7,N)
670 NEXT N
680 A=36 @ A1=0 @ A3=1000 @ T=0
690 FOR N=1 TO 34
700 Z$=GET$(A$(N))
710 D=A-N @ C=2*N-1
720 X1=(34-N)/33
730 FOR M=1 TO C
```

```
740 X2=0 @ X3=0 @ X4=0 @ X5=0
750 X6=0 @ X7=0
760 IF C=1 THEN 850
770 F=(M-1)/(C-1)
780 X2=(1-F)*(1-X1)
790 X3=F*(1-X1)
800 X4=X1*X2
810 X5=X1*X3
820 X6=X2*X3
830 X7=X1*X2*X3
840 A2=0
850 FOR Y=1 TO V1-1
860 P(Y)=X1*B1(1,Y)+X2*B1(2,Y)+X3*B1(3,Y)+X4*B1(4,Y)
870 Q(Y)=X6*B1(5,Y)+X5*B1(6,Y)+X7*B1(7,Y)
880 P(Y)=P(Y)+Q(Y)
890 NEXT Y
900 D6=1000
910 FOR Q=1 TO V1-2
920 FOR Y=Q+1 TO V1-1
930 A2=P(Q)/P(Y)
940 R=(P(Q)-P(Y))/(P(Q)+P(Y)+2)
950 IF R<0 THEN R=-R
960 IF R<D6 THEN D6=R
970 NEXT Y
980 NEXT Q
990 B(N,D)=D6
1000 T=D6
1010 IF T>A1 THEN 1020 ELSE 1030
1020 A1=T @ S1=X1 @ S2=X2 @ S3=X3
1030 IF T<A3 THEN A3=T
1040 D=D+1
1050 NEXT M
1060 DISP N
1070 NEXT N
1080 C=AMAX(B)
1090 D=AMIN(B)
1100 A=A1-A3
1110 L(9)=.9*A+A3
1120 L(7)=.75*A+A3
1130 L(5)=.5*A+A3
1140 G(1)=32 @ G(2)=46 @ G(3)=124
1150 G(4)=90
1160 A=36 @ A3=1
1170 FOR N=1 TO 34
1180 Z$=GET$(A$(N))
1190 D=A-N @ C=2*N-1
1200 FOR M=1 TO C
1210 T=B(N,D)
1220 IF T<A3 THEN A3=T
1230 IF T>L(9) THEN G$=CHR$(G(1)) @ GOTO 1270
1240 IF T>L(7) THEN G$=CHR$(G(2)) @ GOTO 1270
1250 IF T>L(5) THEN G$=CHR$(G(3)) @ GOTO 1270
1260 G$=CHR$(G(4))
1270 Z$[D,D]=G$
1280 D=D+1
1290 NEXT M
1300 Z$[D,D]="\"
1310 SLET A$(N) = Z$
1320 NEXT N
1330 A=AMAX(B)
1340 C=AMAXROW
1350 D=AMAXCOL
1360 Z$=GET$(A$(C))
1370 Z$[D,D]=CHR$(42)
1380 SLET A$(C) = Z$
1390 OUTPUT 10 ;CHR$(15)
1400 PRINTER IS 10,70
1410 FOR N=1 TO 35
1420 Z$=GET$(A$(N))
1430 PRINT Z$
1440 WAIT 1000
1450 NEXT N
```

```
1460 IMAGE 10X,K,8X,K,8X,K,8X,K,8X,K,8X,K
1470 PRINT USING 1460 ; 10,20,30,40,50,60
1480 PRINT @ PRINT
1490 PRINT "MAX SEPARATION FACTOR=";A1
1500 PRINT "MIN SEPARATION FACTOR=";A3
1510 Q1=C1*S1 @ Q4=C4*S2 @ Q7=C7*S3
1520 PRINT "TO OBTAIN MAX SEPARATION FACTOR USE"
1530 PRINT ;Q1;"% MEOH"
1540 PRINT ;Q4;"% CH3CN"
1550 PRINT ;Q7;"% THF"
1560 OUTPUT 10 ;CHR$(14)
1570 PRINTER IS 2
1580 DISP "DO YOU WISH TO FIND COMPOSITION OF A POINT(Y/N) ";
1590 INPUT A$
1600 IF A$="Y" THEN 1610 ELSE 1710
1610 DISP "INPUT ROW THEN COLUMNTO FIND COMPOSITION"
1620 DISP "ROW"
1630 INPUT A9
1640 DISP "COL"
1650 INPUT B9
1660 C9=B9-34+A9
1670 S1=1-(A9-1)/33
1680 C8=(C9-1)/(2*A9-2)
1690 S3=(1-S1)*C8 @ S2=(1-S1)*(1-C8)
1700 GOTO 1510
1710 END
```

What is claimed is:

1. A method for automatically effecting liquid chromatography separations of a multicomponent sample using a mobile phase having three selectivity adjusting solvents and using a liquid chromatograph column having an automatic sampler module for introducing samples into the column comprising the steps of:

selecting three solvents each contributing to a different one of the factors proton acceptor, proton donor, dipole interaction which contribute to total mobile phase selectivity along with a strength adjusting solvent for either reversed phase or normal phase chromatographic separations;

effecting a chromatographic separation of the sample under a gradient condition which adjusts the strength of one of said three selectivity adjusting solvents with said strength adjusting solvent;

calculating, based upon the retention time of the last sample component in the gradient run, the binary solvent composition $E_1$ necessary to obtain the desired retention factor $k'$ in an isocratic separation;

calculating the equivalent mobile phase strengths for the remaining two binary solvent mobile phases;

effecting successive separations of the sample and each component thereof utilizing the three defined solvents at their calculated strengths;

utilizing blends of the fixed ratios of the three defined binary solvents to provide an overlapping resolution map and to determine the optimum mobile phase composition for obtaining a chosen selectivity; and effecting a sample separation using such optimum composition.

2. The method set forth in claim 1 wherein the optimum composition is selected to provide a chosen resolution level.

3. The method set forth in claim 1 wherein binary solvent composition $E_1$ is calculated by determining the logarithmic isocratic retention factor $L_1$ using the formula $$L_1 = Ax^3 + Bx^2 + Cx - D$$

where

A=0.002
B=−0.061
C=0.630
D=0.577 and X=largest retention time in the gradient run, then calculating the slope $D_2$ (a line defining the relationship between such retention factor $L_1$ and solvent strength by the relation $D_2 = -0.01613 + (0.007L_1)$) and finally determining the isocratic first mobile phase strength $E_1$ necessary to obtain the desired $k'$ solving the relation $$E_1 = \frac{\log(\text{desired } k') - L_1}{D_2}.$$

* * * * *